United States Patent
Mashita et al.

(10) Patent No.: US 9,528,950 B2
(45) Date of Patent: Dec. 27, 2016

(54) METHOD FOR EVALUATING MODULUS OF REPULSION ELASTICITY, HARDNESS AND ENERGY LOSS OF POLYMER MATERIAL

(75) Inventors: Ryo Mashita, Kobe (JP); Hiroyuki Kishimoto, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 247 days.

(21) Appl. No.: 14/237,915

(22) PCT Filed: Sep. 11, 2012

(86) PCT No.: PCT/JP2012/073210
§ 371 (c)(1),
(2), (4) Date: Feb. 10, 2014

(87) PCT Pub. No.: WO2013/065405
PCT Pub. Date: May 10, 2013

(65) Prior Publication Data
US 2014/0205068 A1   Jul. 24, 2014

(30) Foreign Application Priority Data

Nov. 1, 2011 (JP) .................................. 2011-240443
Nov. 18, 2011 (JP) .................................. 2011-253026
Nov. 18, 2011 (JP) .................................. 2011-253027

(51) Int. Cl.
*G01N 23/202* (2006.01)
*G01N 23/201* (2006.01)

(52) U.S. Cl.
CPC .......... *G01N 23/201* (2013.01); *G01N 23/202* (2013.01); *G01N 2223/106* (2013.01);
(Continued)

(58) Field of Classification Search
CPC ................ G01N 2223/1016; G01N 2223/623; G01N 2223/627; G01N 23/201; G01N 23/202
See application file for complete search history.

(56) References Cited

U.S. PATENT DOCUMENTS

2006/0046049 A1   3/2006   Abe et al.

FOREIGN PATENT DOCUMENTS

CN   1793872 A   6/2008
JP   4-370739 A   12/1992
(Continued)

OTHER PUBLICATIONS

Koga et al., New Insight into Hierarchical Structures of Carbon Black Dispersed in Polymer Matrices: A Combined Small-Angle Scattering Study, 2008, Macromolecules, vol. 41, pp. 453-464.*
(Continued)

*Primary Examiner* — David J Makiya
*Assistant Examiner* — John Corbett
(74) *Attorney, Agent, or Firm* — Birch, Stewart, Kolasch & Birch, LLP

(57) ABSTRACT

The present invention provides a method for evaluating the rebound resilience, hardness, or energy loss of polymer materials, capable of sufficiently evaluating the difference in performance between samples with excellent measurement accuracy. The present invention relates to a method for evaluating the rebound resilience, hardness, or energy loss of a polymer material, including irradiating the polymer material with X-rays or neutrons to perform X-ray scattering measurement or neutron scattering measurement.

20 Claims, 8 Drawing Sheets

---

Performing X-ray scattering measurement or neutron scattering measurement of a polymer material to obtain a scattering intensity curve I(q).

↓

Determining a radius of gyration Rg1 by curve fitting Formula 1-2 and Formula 1-3 to the scattering intensity curve I(q).

↓

Evaluating rebound resilience based on the radius of gyration Rg1 using a relationship that the rebound resilience increases as the radius of gyration Rg1 decreases.

(52) U.S. Cl.
CPC ............... *G01N 2223/1016* (2013.01); *G01N 2223/623* (2013.01); *G01N 2223/627* (2013.01)

(56) References Cited

FOREIGN PATENT DOCUMENTS

| JP | 2004-27432 A | 1/2004 |
|---|---|---|
| JP | 2004-132869 A | 4/2004 |
| JP | 2009-46088 A | 3/2009 |
| JP | 2009-263536 A | 11/2009 |
| JP | 2010-181342 A | 8/2010 |
| WO | WO 2004/003080 A1 | 1/2004 |
| WO | WO 2010/090294 A1 | 8/2010 |

OTHER PUBLICATIONS

Kohlbrecher, SASfit: A program for fitting simple structural models to small angle scattering data, Jun. 3, 2010, Paul Scherrer Institute Laboratory for Neutron Scattering (LNS), 358 pages.*

Beaucage, Approximations Leading to a Unified Exponential/Power-Law Approach to Small-angle Scattering, 1995, Journal of Applied Crystallography, vol. 28, pp. 717-728.*

Kohls, Synthesis, characterization and properties of filled polymer systems, 2006, Doctoral Thesis, University of Cincinnati, 225 pages.*

Rajan, Understanding aggregate morphology in colloidal systems through small-angle scattering and reverse Monte Carlo (RMC) simulations, 2008, Master's thesis, University of Cincinnati, 95 pages.*

Fitzgerald, John J. et al., Synthesis and characterization of a fluorinated poly(imide-siloxane) copolymer: a study of physical properties and morphology; Polymer, May 1, 1993, vol. 34, No. 9, pp. 1823-1832.

Krishnamoorti, Ramanan et al., "Structure and Dynamics of Polymer-Layered Silicate Nanocomposites", Chemistry of Materials, vol. 8, No. 8, Jan. 1, 1996, pp. 1728-1734.

Pople, J.A. et al., "Shear-induced orientational order in the hexagonal phase of oxyethylene/oxybutylene diblock copolymer gels", Polymer, vol. 39, No. 20, Sep. 1, 1998, pp. 4891-4896.

Amemiya et al., "Long-term Report: Study on Aggregate Structure of Nanoparticles in Rubber with Time-resolved Two-dimensional Ultra-Small-Angle and Small-Angle X-Ray Scattering", SPring-8 Information, May 2009, vol. 14, No. 2, pp. 149-153 (English abstract only).

Kashiwagura et al., "Measurement of Elastic Constants of MBE Grown (Ga0.5AI0.5)As Mixed Thin Film Crystal by Diffuse X-Ray Scattering", Japanese Journal of Applied Physics, vol. 25, No. 9, Sep. 1986, pp. 1317-1322.

Nakamae et al., "Measurement of the Elastic . . . ", Japanese Journal of Polymer Science and Technology, vol. 42, No. 3, Mar. 1985, pp. 211-217 (English abstract only).

Yuasa et al., "Mattan Hensei SSBR o Mochiita Compound-chu deno Filler Gyoshu Kozo to Bunsan Jotai no Kaiseki 2", Elastomer Toronkai Koen Yoshishu, vol. 21, Dec. 2009, pp. 41-43.

JIS K6253, "Rubber, vulcanized or thermoplastic—Determination of Hardness", 2006, pp. 822-855, Not in English—considered to the extent possible.

JIS K6255, "Rubber, vulcanized or thermoplastic—Determination of rebound resilience", 2013, 26 pages, Not in English—considered to the extent possible.

Kishimoto, "Gomu Fukugo Zairyo eno Hoshako no Oyo to Kaiseki", AFMc, 2008, No. 32, RCTF Preprints, pp. 35-40, Not in English—considered to the extent possible.

Shinohara et al., "Small-angle X-ray Scattering of Filled Rubber", Spring-8, vol. 27, No. 4, Apr. 2007, pp. 83-90, Not in English—considered to the extent possible.

* cited by examiner

Performing X-ray scattering measurement or neutron scattering measurement of a polymer material to obtain a scattering intensity curve I(q).

Determining a radius of gyration Rg1 by curve fitting Formula 1-2 and Formula 1-3 to the scattering intensity curve I(q).

Evaluating rebound resilience based on the radius of gyration Rg1 using a relationship that the rebound resilience increases as the radius of gyration Rg1 decreases.

FIG. 4

Performing X-ray scattering measurement or neutron scattering measurement of a polymer material to obtain a scattering intensity curve I(q).

Determining a radius of gyration Rg of 1 nm to 100 μm by curve fitting Formula 2-2 and Formula 2-3 to the scattering intensity curve I(q).

Evaluating hardness based on the radius of gyration Rg using a relationship that the hardness increases as the radius of gyration Rg decreases.

FIG. 5

Performing X-ray scattering measurement or neutron scattering measurement of a polymer material to obtain a scattering intensity curve I(q).

Determining a radius of gyration Rg of 1 nm to 100 μm by curve fitting Formula 3-2 and Formula 3-3 to the scattering intensity curve I(q).

Evaluating energy loss based on the radius of gyration Rg using a relationship that the energy loss decreases as the radius of gyration Rg decreases.

FIG. 7

Performing X-ray scattering measurement or neutron scattering measurement of a polymer material to obtain a scattering intensity curve I(q).

↓

Determining a number N per unit volume of scatterers having a radius of gyration Rg of 1 nm to 100 μm by curve fitting Formula 3-2 to Formula 3-5 to the scattering intensity curve I(q).

↓

Evaluating energy loss based on the number N using a relationship that the energy loss decreases as the number N decreases.

FIG. 8

METHOD FOR EVALUATING MODULUS OF REPULSION ELASTICITY, HARDNESS AND ENERGY LOSS OF POLYMER MATERIAL

TECHNICAL FIELD

The present invention relates to a method for evaluating the rebound resilience of polymer materials, a method for evaluating the hardness of polymer materials, and a method for evaluating the energy loss in polymer materials.

BACKGROUND ART

Methods for evaluating the rebound resilience of polymer materials are defined in JIS K6255 "Rubber, vulcanized or thermoplastic—Determination of rebound resilience". Generally used is a lupke-type rebound resilience test where a pendulum is used to calculate values of rebound resilience from the height from which the pendulum is dropped and the height to which the pendulum rebounds (see Non-Patent Literature 1).

In the case of using a lupke-type rebound resilience tester, the lower the energy loss during the swinging movement of the pendulum, the higher the experimental accuracy. JIS K6255 defines testing methods for determining the period of free oscillation of the pendulum and the logarithmic decrement as a measure of accuracy of measured values.

However, such physical evaluation methods, as by dropping a pendulum made of metal or the like onto a polymer material, give very large errors, failing to provide satisfactory measurement accuracy. Another problem is that, in cases where the difference in value between samples is small, the difference cannot be evaluated with good reproducibility. In addition, the methods include no method for evaluating the molecular structure in detail.

Meanwhile, for polymer materials such as rubber materials, the hardness is an important physical quantity that affects various properties of products. For example, the hardness of tires, which are rubber products, is closely linked to the properties including handling stability and the performance on ice and snow. Widely known methods for measuring the hardness of rubber products are in conformity with JIS K6253 (see Non-Patent Literature 2).

However, the measurement methods using a JIS hardness tester give large errors, failing to provide satisfactory measurement accuracy. Another problem is that, in cases where the difference in value between samples is small, the difference cannot be evaluated with good reproducibility.

Furthermore, for polymer materials such as rubber materials, the energy loss is also an important physical quantity that affects various properties of products. For example, the energy loss in tires, which are rubber products, is closely linked to fuel economy and grip performance. Widely used methods for evaluating the energy loss in polymer materials are to evaluate the loss tangent (tan δ) which can be determined by dynamic viscoelasticity analysis (see Patent Literature 1).

However, the methods for evaluating the energy loss based on the loss tangent give large errors, failing to provide satisfactory measurement accuracy. Another problem is that, in cases where the difference in value between samples is small, the difference cannot be evaluated with good reproducibility.

CITATION LIST

Non Patent Literature

Non-Patent Literature 1: JIS K6255 "Rubber, vulcanized or thermoplastic—Determination of rebound resilience"

Non-Patent Literature 2: JIS K6253 "Rubber, vulcanized or thermoplastic—Determination of hardness"

Patent Literature

Patent Literature 1: JP 2009-46088 A

SUMMARY OF INVENTION

Technical Problem

The present invention aims to provide a method for evaluating the rebound resilience of polymer materials, capable of solving the above problems and of sufficiently evaluating the difference in performance between samples with excellent measurement accuracy.

The present invention aims to provide a method for evaluating the hardness of polymer materials, capable of solving the above problems and of sufficiently evaluating the difference in performance between samples with excellent measurement accuracy.

The present invention aims to provide a method for evaluating the energy loss in polymer materials, capable of solving the above problems and of sufficiently evaluating the difference in performance between samples with excellent measurement accuracy.

Solution to Problem

A first aspect of the present invention relates to a method for evaluating rebound resilience of a polymer material, including irradiating the polymer material with X-rays or neutrons to perform X-ray scattering measurement or neutron scattering measurement.

In the first aspect of the present invention, preferably, the X-ray scattering measurement is small-angle X-ray scattering measurement and the neutron scattering measurement is small-angle neutron scattering measurement.

In the first aspect of the present invention, the polymer material preferably contains at least one metal-coordinating functional group in its molecular structure.

In the first aspect of the present invention, the measurement is preferably performed using the X-rays or neutrons under conditions where q defined by the following Formula 1-1 is in a range of not more than 10 nm$^{-1}$:

[Math. 1]

$$q = \frac{4\pi \sin(\theta/2)}{\lambda} \qquad \text{Formula 1-1}$$

wherein θ is a scattering angle; and λ is a wavelength of X-rays or neutrons.

In the first aspect of the present invention, the rebound resilience is preferably evaluated based on a radius of gyration $R_{g1}$ determined by curve fitting the following Formula 1-2 and Formula 1-3 to a scattering intensity curve $I_{(q)}$ obtained by the X-ray scattering measurement or neutron scattering measurement:

[Math. 2]

$$I_{(q)} = P_1\left[\left\{\mathrm{erf}\left(\frac{qR_{g0}}{\sqrt{6}}\right)^3 / q\right\}\right]^{D_{f1}} \exp\left(\frac{-q^2 R_{g1}^2}{3}\right) + \quad \text{Formula 1-2}$$

$$G_1 \exp\left(\frac{-q^2 R_{g1}^2}{3}\right) + P_2\left[\left\{\mathrm{erf}\left(\frac{qR_{g1}}{\sqrt{6}}\right)^3 / q\right\}\right]^{D_{f2}},$$

$$\mathrm{erf}(z) = \frac{2}{\sqrt{\pi}} \int_0^z e^{-t^2} dt \quad \text{Formula 1-3}$$

wherein $P_1$, $P_2$, $G_1$, $R_{g0}$, $R_{g1}$, $D_{f1}$, and $D_{f2}$ are fitting parameters; q is as defined above; and z and t are any positive numbers.

A second aspect of the present invention relates to a method for evaluating hardness of a polymer material, including irradiating the polymer material with X-rays or neutrons to perform X-ray scattering measurement or neutron scattering measurement.

In the second aspect of the present invention, preferably, the X-ray scattering measurement is small-angle X-ray scattering measurement and the neutron scattering measurement is small-angle neutron scattering measurement.

In the second aspect of the present invention, the polymer material is preferably a rubber material formed from one or more conjugated diene compounds. The rubber material is preferably a rubber material for tires.

In the second aspect of the present invention, an embodiment of the method for evaluating hardness of a polymer material is preferred in which the measurement is performed using the X-rays or neutrons under conditions where q defined by the following Formula 2-1 is in a range of not more than 10 nm$^{-1}$:

[Math. 3]

$$q = \frac{4\pi \sin(\theta/2)}{\lambda} \quad \text{Formula 2-1}$$

wherein $\theta$ is a scattering angle; and $\lambda$ is a wavelength of X-rays or neutrons.

In the second aspect of the present invention, an embodiment of the method for evaluating hardness of a polymer material is preferred in which the hardness is evaluated based on a radius of gyration $R_g$ of 1 nm to 100 μm determined by curve fitting the following Formula 2-2 and Formula 2-3 to a scattering intensity curve $I_{(q)}$ obtained by the X-ray scattering measurement or neutron scattering measurement:

[Math. 4]

$$I_{(q)} = \quad \text{Formula 2-2}$$

$$\sum_{i=1}^{n}\left(P_i\left[\left\{\mathrm{erf}\left(\frac{qR_{gi}}{\sqrt{6}}\right)^3 / q\right\}\right]^{D_{fi}} \exp\left(\frac{-q^2 R_{g(i+1)}^2}{3}\right) + \right.$$

$$G_i \exp\left(\frac{-q^2 R_{g(i+1)}^2}{3}\right)\right) +$$

$$P_{n+1}\left[\left\{\mathrm{erf}\left(\frac{qR_{g(n+1)}}{\sqrt{6}}\right)^3 / q\right\}\right]^{D_{f(n+1)}},$$

$$\mathrm{erf}(z) = \frac{2}{\sqrt{\pi}} \int_0^z e^{-t^2} dt \quad \text{Formula 2-3}$$

wherein $P_i$, $G_i$, $R_{gi}$, and $D_{fi}$ are fitting parameters; n is an integer; q is as defined above; and z and t are any positive numbers.

In the second aspect of the present invention, an embodiment of the method for evaluating hardness of a polymer material is preferred in which the hardness is evaluated based on a number N per unit volume of scatterers having a radius of gyration $R_g$ of 1 nm to 100 μm determined by curve fitting the following Formula 2-2 to Formula 2-5 to a scattering intensity curve $I_{(q)}$ obtained by the X-ray scattering measurement or neutron scattering measurement:

[Math. 5]

$$I_{(q)} = \quad \text{Formula 2-2}$$

$$\sum_{i=1}^{n}\left(P_i\left[\left\{\mathrm{erf}\left(\frac{qR_{gi}}{\sqrt{6}}\right)^3 / q\right\}\right]^{D_{fi}} \exp\left(\frac{-q^2 R_{g(i+1)}^2}{3}\right) + \right.$$

$$G_i \exp\left(\frac{-q^2 R_{g(i+1)}^2}{3}\right)\right) +$$

$$P_{n+1}\left[\left\{\mathrm{erf}\left(\frac{qR_{g(n+1)}}{\sqrt{6}}\right)^3 / q\right\}\right]^{D_{f(n+1)}},$$

$$\mathrm{erf}(z) = \frac{2}{\sqrt{\pi}} \int_0^z e^{-t^2} dt, \quad \text{Formula 2-3}$$

$$G_i = N_i(\sigma V_i)^2, \quad \text{Formula 2-4}$$

$$V_i = \frac{4}{3}\pi\left(\sqrt{\frac{5}{3}} R_{gi}\right)^3 \quad \text{Formula 2-5}$$

wherein $P_i$, $G_i$, $R_{gi}$, and $D_{fi}$ are fitting parameters; $N_i$ is a number of scatterers per unit volume (N/cm$^3$); $V_i$ is a volume of scatterer having the radius of gyration $R_{gi}$; n is an integer; q is as defined above; z and t are any positive numbers; and σ is a difference in electron density (electron·cm$^{-3}$) between a scatterer and a surrounding matrix material, or a difference in scattering length density (cm$^{-2}$) between a scatterer and a surrounding deuterated solvent.

A third aspect of the present invention relates to a method for evaluating energy loss in a polymer material, including irradiating the polymer material with X-rays or neutrons to perform X-ray scattering measurement or neutron scattering measurement.

In the third aspect of the present invention, preferably, the X-ray scattering measurement is small-angle X-ray scattering measurement and the neutron scattering measurement is small-angle neutron scattering measurement.

In the third aspect of the present invention, the polymer material is preferably a rubber material formed from one or more conjugated diene compounds. The rubber material is preferably a rubber material for tires.

In the third aspect of the present invention, the polymer material is preferably a material in which an amount of at least one of a metal and a metal compound is reduced. The polymer material is also preferably a material in which an amount of at least one of a metal and a metal compound is reduced using an acidic solvent.

In the third aspect of the present invention, an embodiment of the method for evaluating energy loss in a polymer material is preferred in which the measurement is performed using the X-rays or neutrons under conditions where q defined by the following Formula 3-1 is in a range of not more than 10 nm$^{-1}$:

[Math. 6]

$$q = \frac{4\pi \sin(\theta/2)}{\lambda} \quad \text{Formula 3-1}$$

wherein θ is a scattering angle; and λ is a wavelength of X-rays or neutrons.

In the third aspect of the present invention, an embodiment of the method for evaluating energy loss in a polymer material is preferred in which the energy loss is evaluated based on a radius of gyration $R_g$ of 1 nm to 100 μm determined by curve fitting the following Formula 3-2 and Formula 3-3 to a scattering intensity curve $I_{(q)}$ obtained by the X-ray scattering measurement or neutron scattering measurement:

[Math. 7]

$$I_{(q)} = \sum_{i=1}^{n} \left\{ P_i \left[ \left\{ \mathrm{erf}\left(\frac{qR_{gi}}{\sqrt{6}}\right)^3 / q \right\} \right]^{D_{fi}} \exp\left(\frac{-q^2 R_{g(i+1)}^2}{3}\right) + G_i \exp\left(\frac{-q^2 R_{g(i+1)}^2}{3}\right) \right\} + P_{n+1} \left[ \left\{ \mathrm{erf}\left(\frac{qR_{g(n+1)}}{\sqrt{6}}\right)^3 / q \right\} \right]^{D_{f(n+1)}}, \quad \text{Formula 3-2}$$

$$\mathrm{erf}(z) = \frac{2}{\sqrt{\pi}} \int_0^z e^{-t^2} dt \quad \text{Formula 3-3}$$

wherein $P_i$, $G_i$, $R_{gi}$, and $D_{fi}$ are fitting parameters; n is an integer; q is as defined above; and z and t are any positive numbers.

In the third aspect of the present invention, an embodiment of the method for evaluating energy loss in a polymer material is preferred in which the energy loss is evaluated based on a number N per unit volume of scatterers having a radius of gyration $R_g$ of 1 nm to 100 μm determined by curve fitting the following Formula 3-2 to Formula 3-5 to a scattering intensity curve $I_{(q)}$ obtained by the X-ray scattering measurement or neutron scattering measurement:

[Math. 5]

$$I_{(q)} = \sum_{i=1}^{n} \left\{ P_i \left[ \left\{ \mathrm{erf}\left(\frac{qR_{gi}}{\sqrt{6}}\right)^3 / q \right\} \right]^{D_{fi}} \exp\left(\frac{-q^2 R_{g(i+1)}^2}{3}\right) + G_i \exp\left(\frac{-q^2 R_{g(i+1)}^2}{3}\right) \right\} + P_{n+1} \left[ \left\{ \mathrm{erf}\left(\frac{qR_{g(n+1)}}{\sqrt{6}}\right)^3 / q \right\} \right]^{D_{f(n+1)}}, \quad \text{Formula 3-2}$$

$$\mathrm{erf}(z) = \frac{2}{\sqrt{\pi}} \int_0^z e^{-t^2} dt, \quad \text{Formula 3-3}$$

$$G_i = N_i (\sigma V_i)^2, \quad \text{Formula 3-4}$$

$$V_i = \frac{4}{3}\pi \left(\sqrt{\frac{5}{3}} R_{gi}\right)^3 \quad \text{Formula 3-5}$$

wherein $P_i$, $G_i$, $R_{gi}$, and $D_{fi}$ are fitting parameters; $N_i$ is a number of scatterers per unit volume (N/cm$^3$); $V_i$ is a volume of scatterer having the radius of gyration $R_{gi}$; n is an integer; q is as defined above; z and t are any positive numbers; and σ is a difference in electron density (electron·cm$^{-3}$) between a scatterer and a surrounding matrix material, or a difference in scattering length density (cm$^{-2}$) between a scatterer and a surrounding deuterated solvent.

Advantageous Effects of Invention

Since the first aspect of the present invention relates to a method for evaluating rebound resilience, including irradiating a polymer material with X-rays to perform X-ray scattering measurement, the method makes it possible to reduce the measurement error to a low level and to evaluate the rebound resilience of polymer materials with high measurement accuracy. The method of the first aspect can also accurately evaluate the difference in rebound resilience between different samples between which the difference in performance cannot be evaluated with good reproducibility by conventional evaluation methods.

Since the second aspect of the present invention relates to a method for evaluating hardness, including irradiating a polymer material with X-rays or neutrons to perform X-ray scattering measurement or neutron scattering measurement, the method makes it possible to reduce the measurement error to a low level and to evaluate the hardness of polymer materials with high measurement accuracy. The method of the second aspect can also accurately evaluate the difference in hardness between different samples between which the difference in performance cannot be evaluated with good reproducibility by the JIS hardness tester.

Since the third aspect of the present invention relates to a method for evaluating energy loss, including irradiating a polymer material with X-rays or neutrons to perform X-ray scattering measurement or neutron scattering measurement, the method makes it possible to reduce the measurement error to a low level and to evaluate the energy loss in polymer materials with high measurement accuracy. The method of the third aspect can also accurately evaluate the difference in energy loss between different samples between which the difference in performance cannot be evaluated with good reproducibility by dynamic viscoelasticity analysis and the like.

BRIEF DESCRIPTION OF THE DRAWINGS

FIG. 3-1 is one example of scattering intensity curves of samples of Examples 3-1 to 3-6 obtained by SAXS measurement.

FIG. 3-2 is one example of scattering intensity curves of samples of Examples 3-7 to 3-10 obtained by SANS measurement.

FIG. 3-3 is one example of scattering intensity curves of samples of Examples 3-11 to 3-13 obtained by SAXS measurement.

FIG. 4 is a flowchart illustrating a method of evaluating rebound resilience of a polymer material according to one embodiment of the present invention.

FIG. 5 is a flowchart illustrating a method of evaluating rebound resilience of a polymer material according to another embodiment of the present invention.

FIG. 7 is a flowchart illustrating a method of evaluating rebound resilience of a polymer material according to another embodiment of the present invention.

FIG. 8 is a flowchart illustrating a method of evaluating rebound resilience of a polymer material according to another embodiment of the present invention.

DESCRIPTION OF EMBODIMENTS

Figure 1:
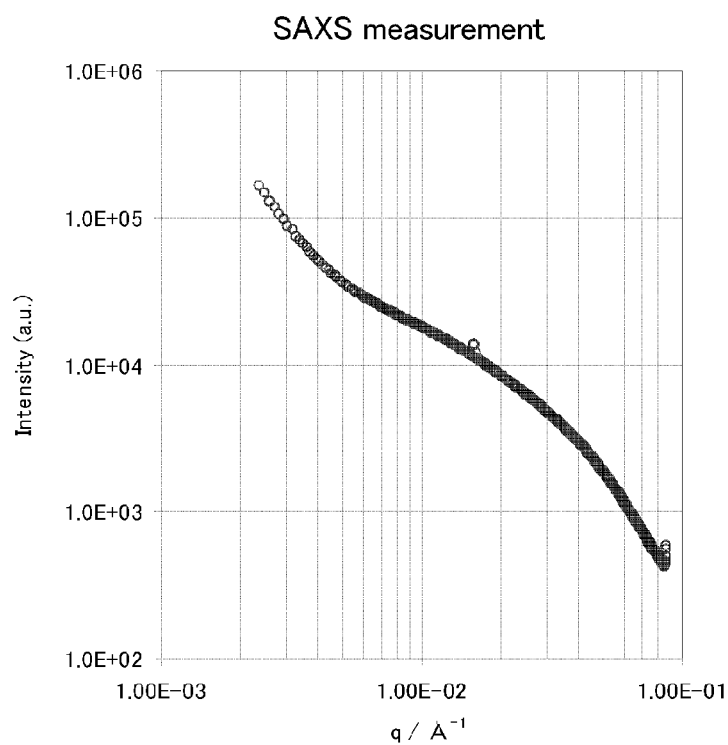
FIG. 1 is a scattering intensity curve of a sample of Example 1-1 obtained by SAXS measurement.

The first aspect of the present invention relates to a method for evaluating rebound resilience of a polymer material, including irradiating the polymer material with X-rays or neutrons to perform X-ray scattering measurement.

For example, the measurement of small-angle X-ray or neutron scattering can be performed on a metal atom-containing polymer material to calculate the radius of gyration of a cluster formed by aggregation of the metal atoms in the material. The method of the first aspect of the present invention has been completed on the basis of the finding that this radius of gyration is highly correlated with rebound resilience and that the smaller the radius of gyration, the higher the rebound resilience. Thus, X-ray scattering or neutron scattering measurement can be performed on a polymer material to evaluate the rebound resilience of the material. The reason why the radius of gyration shows correlation with rebound resilience has not clearly been revealed. It is considered that metal atoms are better dispersed as the radius of gyration of the cluster decreases. Consequently, presumably, the energy loss is reduced and thus the rebound resilience is increased.

In the first aspect of the present invention, the X-ray scattering measurement for evaluating the rebound resilience of a polymer material may suitably be small-angle X-ray scattering (SAXS) measurement (scattering angle: typically 10 degrees or smaller) wherein a polymer material is irradiated with X-rays to measure the scattering intensity. In the small-angle X-ray scattering, structural information of a substance can be obtained by measuring the X-rays scattered at small scattering angles among the scattered X-rays resulting from the irradiation of the substance with X-rays. In this way, ordered structures on the order of a few nanometers (e.g., microphase-separated structures) of polymer materials can be analyzed.

In order to obtain detailed molecular structure information, the SAXS measurement should desirably measure an X-ray scattering profile with a high S/N ratio. For this reason, the X-rays radiated from a synchrotron preferably have a brilliance of at least $10^{10}$ (photons/s/mrad$^2$/mm$^2$/0.1% bw). The symbol bw represents the band width of X-rays radiated from a synchrotron. Examples of such synchrotrons include the beamline BL40B2 of the large synchrotron radiation facility "SPring-8" belonging to Japan Synchrotron Radiation Research Institute.

The brilliance (photons/s/mrad$^2$/mm$^2$/0.1% bw) of the X-rays is preferably $10^{10}$ or higher, and more preferably $10^{12}$ or higher. The upper limit thereof is not particularly limited, and the X-ray intensity used is preferably low enough not to cause radiation damage.

The number of photons (photons/s) in the X-rays is preferably $10^7$ or more, and more preferably $10^9$ or more. The upper limit thereof is not particularly limited, and the X-ray intensity used is preferably low enough not to cause radiation damage.

In the first aspect of the present invention, the neutron scattering measurement for evaluating the rebound resilience of a polymer material may suitably be small-angle neutron scattering (SANS) measurement (scattering angle: typically 10 degrees or smaller) wherein a polymer material is irradiated with neutrons to measure the scattering intensity. In the small-angle neutron scattering, structural information of a substance can be obtained by measuring the neutrons scattered at small scattering angles among the scattered neutrons resulting from the irradiation of the substance with neutrons. In this way, ordered structures on the order of a few nanometers (e.g., microphase-separated structures) of polymer materials can be analyzed.

The SANS measurement may utilize a known magnetic structure-based technique or deuteration technique. In the case of using a deuteration technique, for example, a polymer material is swollen in a deuterated solvent, and the polymer material in equilibrium in the deuterated solvent is irradiated with neutrons to measure the scattering intensity. Examples of the deuterated solvents for swelling polymer materials include heavy water, deuterated hexane, deuterated toluene, deuterated chloroform, deuterated methanol, deuterated DMSO (($D_3C)_2S=O$), deuterated tetrahydrofuran, deuterated acetonitrile, deuterated dichloromethane, deuterated benzene, and deuterated N,N-dimethylformamide.

The neutrons to be used in the neutron scattering measurement such as SANS can be obtained from, for example, the SANS-J beamline at the JRR-3 research reactor belonging to Japan Atomic Energy Agency, Independent Administrative Agency.

The flux density (neutrons/cm$^2$/s) of the neutrons is preferably $10^3$ or higher, and more preferably $10^4$ or higher, because then a neutron scattering profile with a high S/N ratio is obtained as is the case with the SAXS measurement. The upper limit thereof is not particularly limited, and the neutron flux density used is preferably low enough not to cause radiation damage.

Since the measurement is required to measure finer and finer molecular structures of polymer materials, the measurement is preferably performed using the X-rays or neutrons under conditions where q defined by the following Formula 1-1 is in the range of not more than 10 nm$^{-1}$. This q range (nm$^{-1}$) is desirable because a greater numerical value provides finer pieces of information. Thus, the q is more preferably in the range of not more than 20 nm$^{-1}$.

[Math. 9]

$$q = \frac{4\pi \sin(\theta/2)}{\lambda} \qquad \text{Formula 1-1}$$

wherein θ is a scattering angle; and λ is a wavelength of X-rays or neutrons.

The X-rays scattered in the SAXS measurement are detected by an X-ray detector, and an image is then generated by an image processor or the like using the X-ray detection data from the X-ray detector.

Examples of the X-ray detectors include two-dimensional detectors (e.g. X-ray films, nuclear emulsion plates, X-ray image pickup tubes, X-ray fluorescent amplifiers, X-ray image intensifiers, X-ray imaging plates, X-ray CCDs, and X-ray amorphous materials), and line sensor one-dimensional detectors. The X-ray detector may be appropriately selected according to the type and the conditions of a polymer material to be analyzed.

The image processor may appropriately be an ordinary one that can generate X-ray scattering images based on X-ray detection data from an X-ray detector.

The SANS measurement can also be performed based on the same principle as in the SAXS measurement; the neutrons scattered are detected by a neutron detector, and an image is then generated by an image processor or the like using the neutron detection data from the neutron detector. Here, as described above, the neutron detector may be a known two-dimensional detector or one-dimensional detector, and the image processor may be a known one that can generate neutron scattering images. These devices may be appropriately selected.

The polymer material in the first aspect of the present invention is not particularly limited and may be any conventionally known polymer material. Examples thereof include rubber materials formed from one or more conjugated diene compounds, and composite materials formed by combining any of the rubber materials with one or more resins. The conjugated diene compound is not particularly limited, and may be a known compound such as isoprene or butadiene.

Examples of such rubber materials include polymers containing a double bond, including natural rubber (NR), isoprene rubber (IR), butadiene rubber (BR), styrene-butadiene rubber (SBR), acrylonitrile-butadiene rubber (NBR), chloroprene rubber (CR), butyl rubber (IIR), halogenated butyl rubber (X-IIR), and styrene-isoprene-butadiene rubber (SIBR). The polymer material such as a rubber material or a composite material may contain one or more modifying groups such as a hydroxy group and an amino group.

The resin is not particularly limited, and examples thereof include those generally used in the rubber industry, including petroleum resins such as C5 aliphatic petroleum resins and cyclopentadiene petroleum resins.

The polymer material may suitably be, for example, a rubber material or composite material, which contains at least one metal-coordinating functional group in its molecular structure. Here, any metal-coordinating functional group may be used and examples thereof include functional groups containing a metal-coordinating atom such as oxygen, nitrogen, or sulfur. Specific examples include a dithiocarbamate group, a phosphate group, a carboxylate group, a carbamate group, a dithioate group, an aminophosphate group, and a thiol group. The polymer material may contain only one or two or more types of functional groups mentioned above.

Examples of metals that can coordinate to the functional group(s) include Fe, Cu, Ag, Co, Mn, Ni, Ti, V, Zn, Mo, W, Os, Mg, Ca, Sr, Ba, Al, and Si. For example, in the case of a polymer material that includes a compound containing such a metal atom ($M_1$) and also contains a metal-coordinating functional group (such as —COO), each —COO$M_1$ binds to one another by coordinate bonds, resulting in overlapping of many —COO$M_1$ groups and thereby forming clusters of aggregated metal atoms. The amount of the metal atom ($M_1$) is preferably 0.01 to 200 parts by mass per 100 parts by mass of the polymer component of the polymer material.

The polymer material may suitably be a rubber material or a composite material, which contains a filler. Examples of the fillers include carbon black and silica; and $mM_2 \cdot xSiO_y \cdot zH_2O$ wherein $M_2$ represents at least one metal selected from the group consisting of aluminum, calcium, magnesium, titanium and zirconium, or represents an oxide, hydroxide, hydrate, or carbonate of the metal; m represents a number of 1 to 5; x represents a number of 0 to 10; y represents a number of 2 to 5; and z represents a number of 0 to 10.

Specific examples of the fillers represented by $mM_2 \cdot xSiO_y \cdot zH_2O$ include aluminum hydroxide ($Al(OH)_3$), alumina ($Al_2O_3$, $Al_2O_3 \cdot 3H_2O$ (hydrate)), clay ($Al_2O_3 \cdot 2SiO_2$), kaolin ($Al_2O_3 \cdot 2SiO_2 \cdot 2H_2O$), pyrophyllite ($Al_2O_3 \cdot 4SiO_2 \cdot H_2O$), bentonite ($Al_2O_3 \cdot 4SiO_2 \cdot 2H_2O$), aluminum silicate (e.g. $Al_2SiO_5$, $Al_4(SiO_2)_3 \cdot 5H_2O$), aluminum calcium silicate ($Al_2O_3 \cdot CaO \cdot 2SiO_2$), calcium hydroxide ($Ca(OH)_2$), calcium oxide (CaO), calcium silicate ($Ca_2SiO_4$), magnesium calcium silicate ($CaMgSiO_4$), magnesium hydroxide ($Mg(OH)_2$), magnesium oxide (MgO), talc ($MgO \cdot 4SiO_2H_2O$), attapulgite ($5MgO \cdot 8SiO_2 \cdot 9H_2O$), aluminum magnesium oxide ($MgO \cdot Al_2O_3$), titanium white ($TiO_2$), and titanium black ($Ti_nO_{2n-1}$). In a polymer material containing such a filler, the filler particles are aggregated to form a cluster. The amount of the filler is preferably 10 to 200 parts by mass per 100 parts by mass of the polymer component of the polymer material.

The rubber material or composite material may contain any of other compounding agents generally used in the rubber industry (e.g., silane coupling agents, zinc oxide, stearic acid, various antioxidants, oils, waxes, vulcanization agents, vulcanization accelerators, cross-linkers, and the like). Such a rubber material or composite material may be prepared by a known kneading process. Examples of such rubber materials and composite materials include those used as rubber materials for tires.

The following will specifically describe the analysis of a scattering intensity curve obtained by the X-ray scattering measurement or neutron scattering measurement of a polymer material.

For example, a scattering intensity curve obtained by the SAXS measurement or SANS measurement of a polymer material containing both a metal atom and a metal-coordinating functional group can be analyzed as follows, thereby determining the radius of gyration ($R_{g1}$).

The scattering intensity curve $I_{(q)}$ obtained by SAXS or SANS measurement as shown in FIG. 1, for example, is curve fitted with the following Formula 1-2 and Formula 1-3, and the fitting parameters are then determined by least squares.

[Math. 10]

$$I_{(q)} = P_1 \left[ \left\{ \mathrm{erf}\left(\frac{qR_{g0}}{\sqrt{6}}\right)^3 \Big/ q \right\} \right]^{D_{f1}} \exp\left(\frac{-q^2 R_{g1}^2}{3}\right) + G_1 \exp\left(\frac{-q^2 R_{g1}^2}{3}\right) + P_2 \left[ \left\{ \mathrm{erf}\left(\frac{qR_{g1}}{\sqrt{6}}\right)^3 \Big/ q \right\} \right]^{D_{f2}},$$

Formula 1-2

-continued $$\mathrm{erf}(z) = \frac{2}{\sqrt{\pi}} \int_0^z e^{-t^2} dt \qquad \text{Formula 1-3}$$

wherein $P_1$, $P_2$, $G_1$, $R_{g0}$, $R_{g1}$, $D_{f1}$, and $D_{f2}$ are fitting parameters; q is as defined above; and z and t are any positive numbers.

The fitting parameter $R_{g1}$ among the fitting parameters determined is the radius of gyration of a molecular structure with a size of a few nanometers to several tens of nanometers, and is presumed to correspond to the radius of gyration of a cluster formed by aggregation of metal atoms. Since the radius of gyration $R_{g1}$ highly correlates with rebound resilience, i.e., the smaller the $R_{g1}$, the higher the rebound resilience, as mentioned above, a molecular structure with a size of a few nanometers to several tens of nanometers is considered to have a great influence on rebound resilience. Thus, the determination of $R_{g1}$ by X-ray scattering measurement such as SAXS or by neutron scattering measurement such as SANS can be used to evaluate the rebound resilience of polymer materials.

Next, the second aspect of the present invention relates to a method for evaluating hardness of a polymer material, including irradiating the polymer material with X-rays or neutrons to perform X-ray scattering measurement or neutron scattering measurement.

For example, the measurement of small-angle X-ray or neutron scattering can be performed on a metal atom-containing polymer material or a filler (e.g. silica)-containing polymer material to calculate the radius of gyration $R_g$ of a cluster with a size of 1 nm to 100 μm, which is formed by aggregation of metal atoms or filler particles in the material. The method of the second aspect of the present invention has been completed on the basis of the finding that this radius of gyration $R_g$ is highly correlated with hardness and that the smaller the $R_g$, the higher the hardness, as well as the finding that the number N of scatterers having a radius of gyration $R_g$ of 1 nm to 100 μm is highly correlated with hardness and that the greater the number N, the higher the hardness. Thus, X-ray scattering or neutron scattering measurement can be performed on a polymer material to evaluate the hardness of the material.

The reasons why the radius of gyration $R_g$ and the number N of scatterers show correlation with hardness have not clearly been revealed. It is considered that the clusters are densely packed as the radius of gyration $R_g$ of the cluster decreases and as the number N of scatterers of the cluster increases. Consequently, presumably, the hardness is increased.

In the second aspect of the present invention, the X-ray scattering measurement for evaluating the hardness of a polymer material may suitably be small-angle X-ray scattering (SAXS) measurement (scattering angle: typically 10 degrees or smaller) wherein a polymer material is irradiated with X-rays to measure the scattering intensity. In the small-angle X-ray scattering, structural information of a substance can be obtained by measuring the X-rays scattered at small scattering angles among the scattered X-rays resulting from the irradiation of the substance with X-rays. In this way, ordered structures on the order of a few nanometers (e.g., microphase-separated structures) of polymer materials can be analyzed.

In order to obtain detailed molecular structure information, the SAXS measurement should desirably measure an X-ray scattering profile with a high S/N ratio. For this reason, the X-rays radiated from a synchrotron preferably have a brilliance of at least $10^{10}$ (photons/s/mrad$^2$/mm$^2$/0.1% bw). The symbol bw represents the band width of the X-rays radiated from a synchrotron. Examples of such synchrotrons include the beamlines BL03XU and BL20XU of the large synchrotron radiation facility "SPring-8" belonging to Japan Synchrotron Radiation Research Institute.

In the second aspect of the present invention, the brilliance of the X-rays and the number of photons in the X-rays are preferably as mentioned in the first aspect of the present invention.

In the second aspect of the present invention, the neutron scattering measurement for evaluating the hardness of a polymer material may suitably be small-angle neutron scattering (SANS) measurement (scattering angle: typically 10 degrees or smaller) wherein a polymer material is irradiated with neutrons to measure the scattering intensity. In the small-angle neutron scattering, structural information of a substance can be obtained by measuring the neutrons scattered at small scattering angles among the scattered neutrons resulting from the irradiation of the substance with neutrons. In this way, ordered structures on the order of a few nanometers (e.g., microphase-separated structures) of polymer materials can be analyzed.

The SANS measurement may utilize a known magnetic structure-based technique or deuteration technique, as mentioned in the first aspect of the present invention. Also, the flux density of the neutrons may be as mentioned above.

Since the X-ray or neutron scattering measurement is required to measure finer and finer molecular structures of polymer materials, the measurement is preferably performed using the X-rays or neutrons under conditions where q defined by the following Formula 2-1 is in the range of not more than 10 nm$^{-1}$. This q range (nm$^{-1}$) is desirable because a greater numerical value provides finer pieces of information. Thus, the q is more preferably in the range of not more than 20 nm$^{-1}$.

[Math. 11]

$$q = \frac{4\pi \sin(\theta/2)}{\lambda} \qquad \text{Formula 2-1}$$

wherein θ is a scattering angle; and λ is a wavelength of X-rays or neutrons.

The X-rays scattered in the SAXS measurement and the neutrons scattered in the SANS measurement can be measured based on the same principle as in the first aspect of the present invention.

The polymer material in the second aspect of the present invention is not particularly limited, and examples thereof include those mentioned in the first aspect of the present invention. The amounts of the metal atom ($M_1$) and of the filler are preferably in ranges as mentioned above.

The polymer material may contain any of compounding agents as mentioned in the first aspect of the present invention. Moreover, the polymer material may be prepared by the same process, and may be a rubber material for tires or the like.

The following will specifically describe the analysis of a scattering intensity curve obtained by the X-ray scattering or neutron scattering measurement of a polymer material.

For example, a scattering intensity curve $I_{(q)}$ obtained by the SAXS or SANS measurement of a polymer material containing both a metal atom and a metal-coordinating functional group, or a polymer material containing a filler, can be analyzed as follows, thereby determining the radius of gyration ($R_g$) of a cluster (scatterer) with a size of 1 nm to 100 μm.

Figure 2:
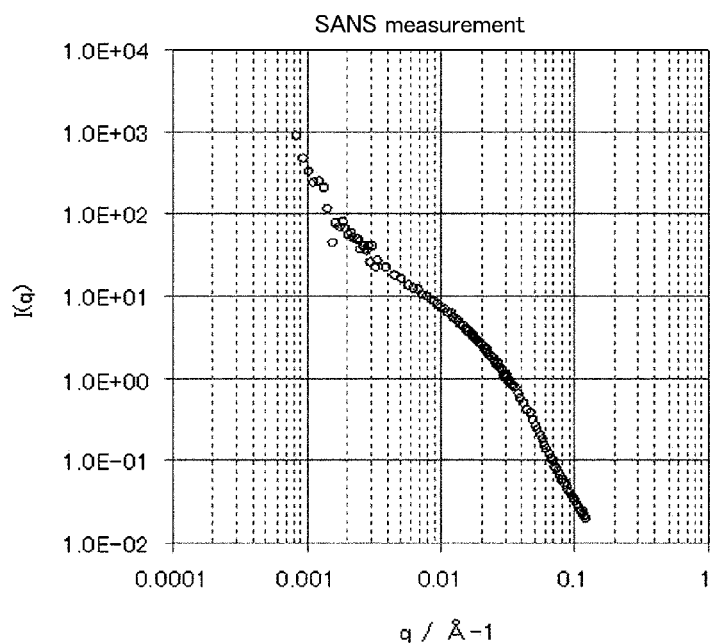
FIG. 2 is one example of scattering intensity curves of samples of Examples 2-1 to 2-4 obtained by SANS measurement.

The scattering intensity curve $I_{(q)}$ obtained by SAXS measurement or the scattering intensity curve $I_{(q)}$ obtained by SANS measurement as shown in FIG. 2, for example, is curve fitted with the following Formula 2-2 and Formula 2-3, and the fitting parameters are then determined by least squares.

[Math. 12]

$$I_{(q)} = \sum_{i=1}^{n} \left\langle P_i \left[ \left\{ \mathrm{erf}\left(\frac{qR_{gi}}{\sqrt{6}}\right)^3 \Big/ q \right\} \right]^{D_{fi}} \exp\left(\frac{-q^2 R_{g(i+1)}^2}{3}\right) + \right. \quad \text{Formula 2-2}$$

$$G_i \exp\left(\frac{-q^2 R_{g(i+1)}^2}{3}\right) \right\rangle +$$

$$P_{n+1}\left[\left\{\mathrm{erf}\left(\frac{qR_{g(n+1)}}{\sqrt{6}}\right)^3 \Big/ q\right\}\right]^{D_{f(n+1)}},$$

$$\mathrm{erf}(z) = \frac{2}{\sqrt{\pi}} \int_0^z e^{-t^2} dt \quad \text{Formula 2-3}$$

wherein $P_i$, $G_i$, $R_{gi}$, and $D_{fi}$ are fitting parameters; n is an integer; q is as defined above; and z and t are any positive numbers.

One of the fitting parameters determined, $R_g$, which is the radius of gyration of a molecular structure with a size of 1 nm to 100 μm, is presumed to correspond to the radius of gyration of a cluster formed by aggregation of metal atoms or filler particles. Since the radius of gyration $R_g$ highly correlates with hardness, i.e., the smaller the $R_g$, the higher the hardness, as mentioned above, $R_g$ is considered to have a great influence on hardness. Thus, the determination of $R_g$ by X-ray scattering measurement such as SAXS, or neutron scattering measurement such as SANS, and the subsequent curve fitting with Formula 2-2 and Formula 2-3 can be used to evaluate the hardness of polymer materials.

In addition, the following will specifically describe another analysis of a scattering intensity curve obtained by the X-ray or neutron scattering measurement of a polymer material.

The scattering intensity curve obtained by SAXS or SANS measurement as mentioned above can be analyzed as follows, thereby determining the number N per unit volume of scatterers having a radius of gyration ($R_g$) of 1 nm to 100 μm.

The scattering intensity curve $I_{(q)}$ obtained by SAXS measurement or the scattering intensity curve $I_{(q)}$ obtained by SANS measurement as shown in FIG. 2, for example, is curve fitted with the following Formula 2-2 to Formula 2-5, and the fitting parameters are then determined by least squares.

[Math. 13]

$$I_{(q)} = \sum_{i=1}^{n} \left\langle P_i \left[ \left\{ \mathrm{erf}\left(\frac{qR_{gi}}{\sqrt{6}}\right)^3 \Big/ q \right\} \right]^{D_{fi}} \exp\left(\frac{-q^2 R_{g(i+1)}^2}{3}\right) + \right. \quad \text{Formula 2-2}$$

$$G_i \exp\left(\frac{-q^2 R_{g(i+1)}^2}{3}\right) \right\rangle +$$

$$P_{n+1}\left[\left\{\mathrm{erf}\left(\frac{qR_{g(n+1)}}{\sqrt{6}}\right)^3 \Big/ q\right\}\right]^{D_{f(n+1)}},$$

$$\mathrm{erf}(z) = \frac{2}{\sqrt{\pi}} \int_0^z e^{-t^2} dt, \quad \text{Formula 2-3}$$

$$G_i = N_i (\sigma V_i)^2, \quad \text{Formula 2-4}$$

$$V_i = \frac{4}{3}\pi \left(\sqrt{\frac{5}{3}} R_{gi}\right)^3 \quad \text{Formula 2-5}$$

wherein $P_i$, $G_i$, $R_{gi}$, and $D_{fi}$ are fitting parameters; $N_i$ is the number of scatterers per unit volume (N/cm³); $V_i$ is the volume of scatterer having the radius of gyration $R_{gi}$; n is an integer; q is as defined above; z and t are any positive numbers; and σ is the difference in electron density (electron·cm⁻³) between the scatterer and a surrounding matrix material, or the difference in scattering length density (cm⁻²) between the scatterer and a surrounding deuterated solvent.

The fitting parameter G among the fitting parameters determined can be used to determine the number N per unit volume of scatterers having a radius of gyration ($R_g$) of 1 nm to 100 μm. In determining the number N, the difference in electron density or in scattering length density between the scatterer and a surrounding matrix material is used. Known values or measured values may be employed as the difference in electron density between a filler (e.g. silica) and a rubber material (e.g. butadiene rubber) or the difference in scattering length density between a scatterer and a surrounding deuterated solvent. More specifically, in the case of the X-ray scattering measurement of a rubber material containing silica as a scatterer (matrix rubber: natural rubber, butadiene rubber, modified butadiene rubber, or the like), the difference σ in electron density may be a value of $3.8 \times 10^{23}$ (electron·cm⁻³). In the case of the neutron scattering measurement of a polymer material containing polybutadiene as a scatterer, which is swollen to equilibrium in deuterated toluene, for example, the difference σ in scattering length density may be a value of $5.22 \times 10^{10}$ (cm⁻²). Since this number N highly correlates with hardness, i.e., the smaller the number N, the higher the hardness, as mentioned above, the number N is considered to have a great influence on hardness. Thus, the determination of the number N by X-ray scattering measurement such as SAXS, or neutron scattering measurement such as SANS, and the subsequent curve fitting with Formula 2-2 to Formula 2-5 can be used to evaluate the hardness of polymer materials.

Subsequently, the third aspect of the present invention relates to a method for evaluating energy loss in a polymer material, including irradiating the polymer material with X-rays or neutrons to perform X-ray scattering measurement or neutron scattering measurement.

For example, the measurement of small-angle X-ray or neutron scattering can be performed on a metal atom-containing polymer material or a filler (e.g. silica)-containing polymer material to calculate the radius of gyration $R_g$ of a cluster with a size of 1 nm to 100 μm, which is formed by aggregation of metal atoms or filler particles in the material. The method of the third aspect of the present invention has been completed on the basis of the finding that this radius of gyration $R_g$ is highly correlated with energy loss and that the smaller the $R_g$, the lower the energy loss, as well as the finding that the number N of scatterers having a radius of gyration $R_g$ of 1 nm to 100 µm is highly correlated with energy loss and that the smaller the number N, the lower the energy loss. Thus, the X-ray scattering or neutron scattering measurement can be performed on a polymer material to evaluate the energy loss in the material.

The reasons why the radius of gyration $R_g$ and the number N of scatterers show correlation with energy loss have not clearly been revealed. It is considered that the clusters are better dispersed as the radius of gyration $R_g$ of the cluster decreases and as the number N of scatterers of the cluster decreases. Consequently, presumably, the energy loss is reduced.

In the third aspect of the present invention, the X-ray scattering measurement for evaluating the energy loss in a polymer material may suitably be small-angle X-ray scattering (SAXS) measurement (scattering angle: typically 10 degrees or smaller) wherein a polymer material is irradiated with X-rays to measure the scattering intensity. In the small-angle X-ray scattering, structural information of a substance can be obtained by measuring the X-rays scattered at small scattering angles among the scattered X-rays resulting from the irradiation of the substance with X-rays. In this way, ordered structures on the order of a few nanometers (e.g., microphase-separated structures) of polymer materials can be analyzed.

In order to obtain detailed molecular structure information, the SAXS measurement should desirably measure an X-ray scattering profile with a high S/N ratio. For this reason, the X-rays radiated from a synchrotron preferably have a brilliance of at least $10^{10}$ (photons/s/mrad²/mm²/0.1% bw). The symbol bw represents the band width of the X-rays radiated from a synchrotron. Examples of such synchrotrons include the beamlines BL03XU and BL20XU of the large synchrotron radiation facility "SPring-8" belonging to Japan Synchrotron Radiation Research Institute.

In the third aspect of the present invention, the brilliance of the X-rays and the number of photons in the X-rays are preferably as mentioned in the first aspect of the present invention.

In the third aspect of the present invention, the neutron scattering measurement for evaluating the energy loss in a polymer material may suitably be small-angle neutron scattering (SANS) measurement (scattering angle: typically 10 degrees or smaller) wherein a polymer material is irradiated with neutrons to measure the scattering intensity. In the small-angle neutron scattering, structural information of a substance can be Obtained by measuring the neutrons scattered at small scattering angles among the scattered neutrons resulting from the irradiation of the substance with neutrons. In this way, ordered structures on the order of a few nanometers (e.g., microphase-separated structures) of polymer materials can be analyzed.

The SANS measurement may utilize a known magnetic structure-based technique or deuteration technique, as mentioned in the first aspect of the present invention. Also, the flux density of the neutrons may be as mentioned above.

Since the X-ray or neutron scattering measurement is required to measure finer and finer molecular structures of polymer materials, the measurement is preferably performed using the X-rays or neutrons under conditions where q defined by the following Formula 3-1 is in the range of not more than 10 nm$^{-1}$. This q range (nm$^{-1}$) is desirable because a greater numerical value provides finer pieces of information. Thus, the q is more preferably in the range of not more than 20 nm$^{-1}$.

[Math. 14]

$$q = \frac{4\pi \sin(\theta/2)}{\lambda} \qquad \text{Formula 3-1}$$

wherein $\theta$ is a scattering angle; and $\lambda$ is a wavelength of X-rays or neutrons.

The X-rays scattered in the SAXS measurement and the neutrons scattered in the SANS measurement can be measured based on the same principle as in the first aspect of the present invention.

The polymer material in the third aspect of the present invention is not particularly limited, and examples thereof include those mentioned in the first aspect of the present invention. The amounts of the metal atom ($M_1$) and of the filler are preferably in ranges as mentioned above.

The polymer material may contain any of compounding agents as mentioned in the first aspect of the present invention. Moreover, the polymer material may be prepared by the same process, and may be a rubber material for tires or the like.

The following will specifically describe the analysis of a scattering intensity curve obtained by the X-ray or neutron scattering measurement of a polymer material.

As mentioned above, for example, a scattering intensity curve obtained by the SAXS or SANS measurement of a polymer material containing both a metal atom and a metal-coordinating functional group, or a polymer material containing a filler can be analyzed as follows, thereby determining the radius of gyration ($R_g$) of a cluster (scatterer) having a size of 1 nm to 100 µm.

Figures 1, 3:
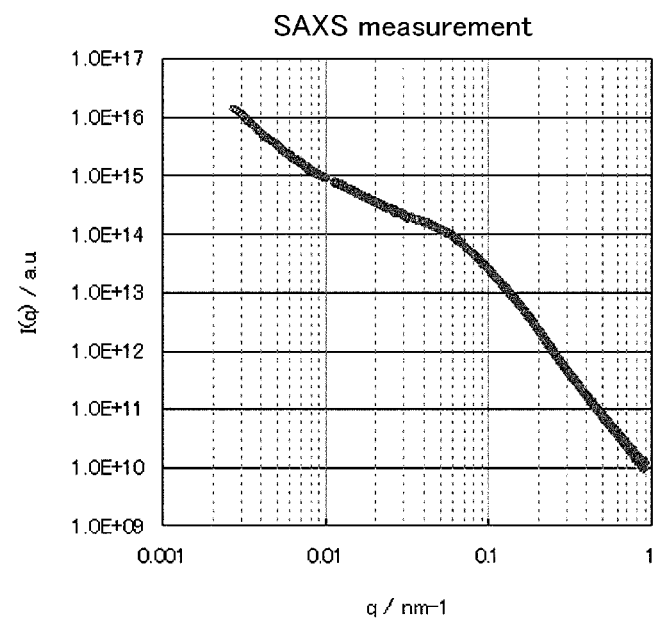
Figures 2, 3:
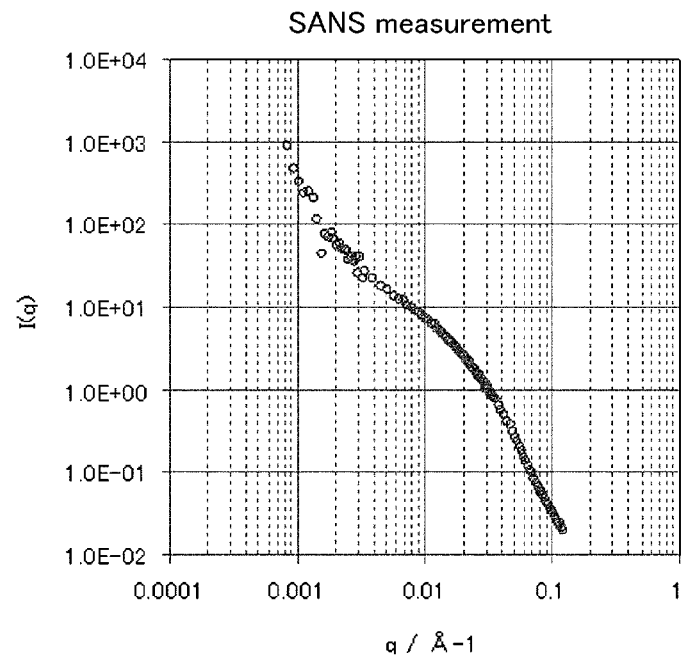
Figure 3:
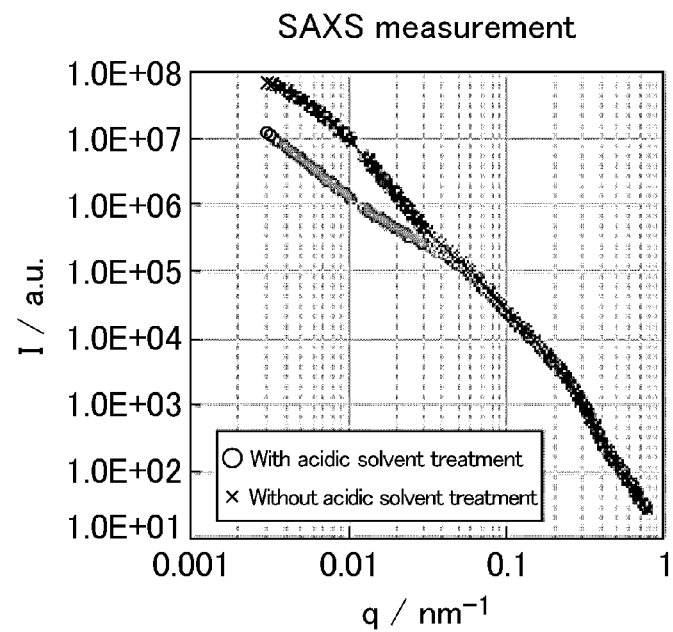
Figure 6:
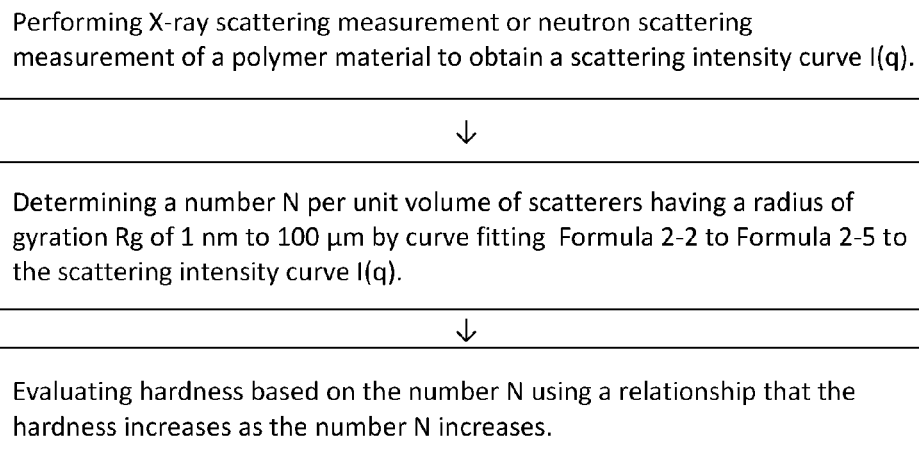
FIG. 6 is a flowchart illustrating a method of evaluating rebound resilience of a polymer material according to another embodiment of the present invention.

The scattering intensity curve $I_{(q)}$ obtained by SAXS or SANS measurement as shown in FIG. 3-1 or 3-2, for example, is curve fitted with the following Formula 3-2 and Formula 3-3, and the fitting parameters are then determined by least squares.

[Math. 15]

$$I_{(q)} = \sum_{i=1}^{n} \left\langle P_i \left[ \left\{ \mathrm{erf}\left(\frac{qR_{gi}}{\sqrt{6}}\right)^3 / q \right\} \right]^{D_{fi}} \exp\left(\frac{-q^2 R_{g(i+1)}^2}{3}\right) + \right. \qquad \text{Formula 3-2}$$

$$G_i \exp\left(\frac{-q^2 R_{g(i+1)}^2}{3}\right) \right\rangle +$$

$$P_{n+1} \left[ \left( \mathrm{erf}\left(\frac{qR_{g(n+1)}}{\sqrt{6}}\right)^3 / q \right) \right]^{D_{f(n+1)}},$$

$$\mathrm{erf}(z) = \frac{2}{\sqrt{\pi}} \int_0^z e^{-t^2} dt \qquad \text{Formula 3-3}$$

wherein $P_i$, $G_i$, $R_{gi}$, and $D_{fi}$ are fitting parameters; n is an integer; q is as defined above; and z and t are any positive numbers.

One of the fitting parameters determined, $R_g$, which is the radius of gyration of a molecular structure with a size of 1 nm to 100 µm, is presumed to correspond to the radius of gyration of a cluster formed by aggregation of metal atoms or filler particles. Since the radius of gyration $R_g$ highly correlates with energy loss, i.e., the smaller the $R_g$, the lower the energy loss, as mentioned above, the $R_g$ is considered to have a great influence on energy loss. Thus, the determination of $R_g$ by X-ray scattering measurement such as SAXS, or neutron scattering measurement such as SANS, and the subsequent curve fitting with Formula 3-2 and Formula 3-3 can be used to evaluate the energy loss in polymer materials.

In addition, the following will specifically describe another analysis of a scattering intensity curve obtained by the X-ray or neutron scattering measurement of a polymer material.

A scattering intensity curve obtained by SAXS or SANS measurement as mentioned above can be analyzed as follows, thereby determining the number N per unit volume of scatterers having a radius of gyration ($R_g$) of 1 nm to 100 μm.

The scattering intensity curve $I_{(q)}$ obtained by SAXS or SANS measurement as shown in FIG. 3-1 or 3-2, for example, is curve fitted with the following Formula 3-2 to Formula 3-5, and the fitting parameters are then determined by least squares.

[Math. 16]

$$I_{(q)} = \sum_{i=1}^{n} \left\{ P_i \left[ \left\{ \text{erf}\left(\frac{qR_{gi}}{\sqrt{6}}\right)^3 / q \right\} \right]^{D_{fi}} \exp\left(\frac{-q^2 R_{g(i+1)}^2}{3}\right) + \right.$$
$$\left. G_i \exp\left(\frac{-q^2 R_{g(i+1)}^2}{3}\right) \right\} +$$
$$P_{n+1}\left[\left(\text{erf}\left(\frac{qR_{g(n+1)}}{\sqrt{6}}\right)^3 / q\right)\right]^{D_{f(n+1)}},$$

Formula 3-2

$$\text{erf}(z) = \frac{2}{\sqrt{\pi}} \int_0^z e^{-t^2} dt,$$

Formula 3-3

$$G_i = N_i(\sigma V_i)^2,$$

Formula 3-4

$$V_i = \frac{4}{3}\pi \left(\sqrt{\frac{5}{3}} R_{gi}\right)^3$$

Formula 3-5 wherein $P_i$, $G_i$, $R_{gi}$, and $D_{fi}$ are fitting parameters; $N_i$ is the number of scatterers per unit volume (N/cm³); $V_i$ is the volume of scatterer having the radius of gyration $R_{gi}$; n is an integer; q is as defined above; z and t are any positive numbers; and σ is the difference in electron density (electron·cm⁻³) between the scatterer and a surrounding matrix material, or the difference in scattering length density (cm⁻²) between the scatterer and a surrounding deuterated solvent.

The fitting parameter G among the fitting parameters determined can be used to determine the number N per unit volume of scatterers having a radius of gyration ($R_g$) of 1 nm to 100 μm. In determining the number N, the difference in electron density or in scattering length density between the scatterer and a surrounding matrix material is used. Known values or measured values may be employed as the difference in electron density or in scattering length density between a filler (e.g. silica) and a rubber material (e.g. butadiene rubber). More specifically, in the case of the X-ray scattering measurement of a rubber material containing silica as a scatterer (matrix rubber: natural rubber, butadiene rubber, modified butadiene rubber, or the like), the difference σ in electron density may be a value of $3.8 \times 10^{23}$ (electron·cm⁻³). In the case of the neutron scattering measurement of a polymer material containing polybutadiene as a scatterer, which is swollen to equilibrium in deuterated toluene, for example, the difference σ in scattering length density may be a value of $5.22 \times 10^{10}$ (cm⁻²). Since this number N highly correlates with energy loss, i.e., the smaller the number N, the lower the energy loss, as mentioned above, the number N is considered to have a great influence on energy loss. Thus, the determination of the number N by X-ray scattering measurement such as SAXS, or neutron scattering measurement such as SANS, and the subsequent curve fitting with Formula 3-2 to Formula 3-5 can be used to evaluate the energy loss in polymer materials.

As mentioned above, the dispersibility of filler (e.g. silica, carbon black) is generally considered to greatly contribute to the energy loss in rubber materials. Thus, in the method for evaluating energy loss in a polymer material of the third aspect of the present invention, the energy loss in a rubber material is evaluated by evaluating the dispersibility of filler. In the case of rubber materials containing a metal and/or a metal compound, such as zinc oxide which is commonly used as a vulcanization aid or the like, some compositions may not be accurately evaluated for dispersibility of filler.

For this reason, the polymer material in the third aspect of the present invention is preferably a polymer material in which the amount of a metal and/or a metal compound is reduced by, for example, a treatment of removing the metal and/or metal compound. This reduces the measurement error to a low level, making it possible to more accurately evaluate the energy loss in the polymer material. Thus, it is possible to more accurately evaluate the difference in energy loss between different samples between which the difference in performance cannot be evaluated with good reproducibility by dynamic viscoelasticity analysis and the like. The amount of a metal and/or a metal compound in the polymer material is preferably as low as possible, and it is preferably 0.5% by mass or less, for example.

The metal and/or metal compound is not particularly limited, and examples thereof include the aforementioned coordinating metals and compounds containing them.

The amount of a metal and/or a metal compound in the polymer material can be reduced by any method that is capable of such a reduction. For example, the method may suitably be performed by extracting a metal and/or a metal compound with an acidic solvent using an apparatus (such as a Soxhlet extractor) that is capable of solvent extraction from a polymer material, to reduce or remove the metal and/or metal compound.

From the viewpoint of extractability, the acidic solvent for extraction may suitably be an acidic solvent mixture of an acid and an organic solvent and/or water, for example. Examples of the acids include mineral acids such as hydrochloric acid, nitric acid, and sulfuric acid. Examples of the organic solvents include acetone and alcohols. The pH of the acidic solvent may be appropriately adjusted in consideration of extractability, and the mixture ratio of an acid, an organic solvent, and water may also be appropriately adjusted.

EXAMPLES

The present invention will be more specifically described with reference to, but not limited to, examples.

The chemicals used in the examples and comparative examples are listed below.
(Reagents)
Cyclohexane: product of KANTO CHEMICAL CO., INC.
Pyrrolidine: product of KANTO CHEMICAL CO., INC.

Divinylbenzene: product of Sigma-Aldrich
n-Butyllithium 1.6 M in hexane: product of KANTO CHEMICAL CO., INC.
Isopropanol: product of KANTO CHEMICAL CO., INC.
Styrene: product of KANTO CHEMICAL CO., INC.
Butadiene: product of TAKACHIHO CHEMICAL INDUSTRIAL CO., LTD.
Tetramethylethylenediamine: product of KANTO CHEMICAL CO., INC.
Modifier: 3-(N,N-dimethylaminopropyl)trimethoxysilane (AZmax. Co)
NR: RSS #3
Silica: product on the market
Silane coupling agent: product on the market
Antioxidant: NOCRAC 6C(N-1,3-dimethylbutyl-N'-phenyl-p-phenylenediamine) (Ouchi Shinko Chemical Industrial Co., Ltd.)
Stearic acid: stearic acid (NOF Corp.)
Aromatic oil: Diana Process AH-24 (Idemitsu Kosan Co., Ltd.)
Wax: SUNNOC wax (Ouchi Shinko Chemical Industrial Co., Ltd)
Zinc oxide: Ginrei R (Toho Zinc Co., Ltd.)
Sulfur: sulfur powder (TSURUMI CHEMICAL INDUSTRY CO., LTD.)
Vulcanization accelerator (1): NOCCELER CZ (Ouchi Shinko Chemical Industrial Co., Ltd.)
Vulcanization accelerator (2): NOCCELER D (Ouchi Shinko Chemical Industrial Co., Ltd.)
BR730: butadiene rubber (JSR Corp.)
SANCELER SR: product of SANSHIN CHEMICAL INDUSTRY CO., LTD.
PERCUMYL D: product of Ouchi Shinko Chemical Industrial Co., Ltd.
TN: 2-naphthalenethiol (Tokyo Chemical Industry Co., Ltd.)
DPDS: diphenyl disulfide (Sumitomo Seika Chemicals Co., Ltd.)
PCTP: pentachlorobenzenethiol (Tokyo Chemical Industry Co., Ltd.)
2,6-DCTP: 2,6-dichlorothiophenol (Tokyo Chemical Industry Co., Ltd.)

Examples 1-1 to 1-5 and Comparative Examples 1-1 to 1-5

Method for Preparing Molded Product

According to each of the compositions shown in Table 1, the materials were kneaded using a Banbury mixer and a roll kneader. Then, the kneaded mixture was press-molded at 170° C. for 20 minutes to provide a molded product.

The rebound resilience (SAXS measurement, metal-piece collision method) and the hardness of the molded products thus obtained were evaluated by the following test methods.

1-1. SAXS Measurement (Examples 1-1 to 1-5)

An about 1-mm-thick plate-like sample (molded product) was mounted on a sample holder, and the sample was irradiated with X-rays at room temperature. A scattering intensity curve $I_{(q)}$ obtained by SAXS measurement was curve fitted with the Formula 1-2 and Formula 1-3, and the fitting parameter $R_{g1}$ was then determined by least squares.

The measurement was repeated 10 times, and a CV (coefficient of variation) value was calculated based on the $R_{g1}$ values obtained. A lower CV value indicates less variation and better accuracy of the measurement.

(SAXS Apparatus)
SAXS: SAXS measurement apparatus provided with the beamline BL40B2 of the large synchrotron radiation facility "SPring-8" belonging to Japan Synchrotron Radiation Research Institute (Measurement Conditions)
Brilliance of X-rays: $5 \times 10^{12}$ photons/s/mrad$^2$/mm$^2$/0.1% bw
Number of photons in X-rays: $2 \times 10^9$ photons/s
Energy of X-rays: 8 keV
Distance between sample and detector: 3 m (Detector)
Image intensifier and CCD camera 1-2. Metal-Piece Collision Method (Comparative Examples 1-1 to 1-5)

A sphere-shaped sample (molded product) was made to collide with a 200-g aluminum hollow cylinder at a speed of 45 m/s. The speeds of the hollow cylinder before and after the collision and the speed of the sample after the collision were measured, and then the rebound resilience of the sample was determined. The measurement was repeated 12 times, and the average value of the data obtained was treated as the rebound resilience of the sample. Based on the data, a CV (coefficient of variation) value was calculated. A lower CV value indicates less variation and better accuracy of the measurement.

1-3. Hardness

The hardness was measured at 25° C. using a Type C durometer in conformity with JIS K6301.

TABLE 1

| | | SAXS (Formula 1-2 and Formula 1-3) | | | | | | | | | |
|---|---|---|---|---|---|---|---|---|---|---|---|
| | | Examples | | | | | Comparative Examples | | | | |
| | | 1-1 | 1-2 | 1-3 | 1-4 | 1-5 | 1-1 | 1-2 | 1-3 | 1-4 | 1-5 |
| Composition | BR730 | 100 | 100 | 100 | 100 | 100 | 100 | 100 | 100 | 100 | 100 |
| | SANCELER SR | 30 | 30 | 30 | 25 | 25 | 30 | 30 | 30 | 25 | 25 |
| | PERCUMYL D | 1 | 0.75 | 0.75 | 1.5 | 0.2 | 1 | 0.75 | 0.75 | 1.5 | 0.2 |
| | TN | 0.52 | — | — | — | — | 0.52 | — | — | — | — |
| | DPDS | — | 0.5 | — | — | — | — | 0.5 | — | — | — |
| | PCTP | — | — | 0.65 | — | — | — | — | 0.65 | — | — |
| | 2,6-DCTP | — | — | — | 0.36 | — | — | — | — | 0.36 | — |
| | Hardness | 67 | 66 | 65 | 64 | 60 | 67 | 66 | 65 | 64 | 60 |

TABLE 1-continued

| | | SAXS (Formula 1-2 and Formula 1-3) | | | | | | | | |
|---|---|---|---|---|---|---|---|---|---|---|
| | | Examples | | | | | Comparative Examples | | | |
| | | 1-1 | 1-2 | 1-3 | 1-4 | 1-5 | 1-1 | 1-2 | 1-3 | 1-4 | 1-5 |
| Method for evaluating rebound resilience | SAXS measurement; CV value | 3.03 | 2.78 | 2.56 | 2.22 | 1.89 | — | — | — | — | — |
| | Metal-piece collision; CV value | — | — | — | — | — | 3.70 | 3.75 | 3.80 | 3.85 | 4.29 |

The results demonstrated that in Examples 1-1 to 1-5, which were based on SAXS measurement, all the compositions had lower CV values and less variation between measurements as compared to the corresponding Comparative Examples 1-1 to 1-5, which were based on a metal-piece collision method, and thus that SAXS measurement can evaluate the rebound resilience with high measurement accuracy and good reproducibility. The results also demonstrated that the examples had greater differences in CV value from one another than the comparative examples and thus that SAXS measurement can accurately measure even the difference in rebound resilience between samples between which the difference in performance is difficult to evaluate by the method of the comparative examples.

Examples 2-1 to 2-4 and Comparative Examples 2-1 to 2-4

Method for Preparing Molded Product

According to each of the compositions shown in Table 2, the materials were kneaded using a Banbury mixer and a roll kneader. Then, the kneaded mixture was press-molded at 170° C. for 20 minutes to provide a molded product.

The hardness of the molded products thus obtained was evaluated by the following SANS measurement and durometer measurement. The results are shown below.

2-1. SANS Measurement (Examples 2-1 to 2-4)

An about 1-mm-thick plate-like sample (molded product) was swollen to equilibrium in deuterated toluene, and mounted on a sample holder, and the sample was then irradiated with neutrons at room temperature. Absolute scattering intensity curves obtained by measuring the sample at distances of 2.5 m and 10 m from the detector and with a focusing lens were combined by least squares. These three curves were combined as follows: the scattering intensity curve obtained by measuring the sample at a distance of 2.5 m from the detector was fixed, and the scattering intensity curves obtained by measuring the sample at a distance of 10 m and with a focusing lens were then shifted. The scattering intensity curve $I_{(q)}$ obtained was curve fitted with Formula 2-2 to Formula 2-5, and the fitting parameter G was then determined by least squares. A value of $5.22 \times 10^{10}$ $(cm^{-2})$ was used as the difference σ in scattering length density of polybutadiene (scatterer, swollen to equilibrium in deuterated toluene) to determine the number N of scatterers (clusters with a radius of gyration $R_g$ of 1 nm to 100 μm) per unit volume. The number N obtained is expressed as an index relative to that of Example 2-1 (=100). A higher index indicates a higher hardness.

(SANS Apparatus)

SANS: SANS measurement apparatus provided with the SANS-J beamline at the JRR-3 research reactor belonging to Japan Atomic Energy Agency, Independent Administrative Agency (Measurement Conditions)

Wavelength of neutrons: 6.5 Å

Flux density of neutrons: $9.9 \times 10^7$ neutrons/$cm^2$/s

Distance between sample and detector: 2.5 m and 10 m (in order to obtain the information at smaller angles, the sample was also measured at a distance of 10 m from the detector, using a focusing lens.)

(Detector)

Two-dimensional detector ($^3$He two-dimensional detector and two-dimensional photomultiplier+ZnS/$^6$LiF detector)

2-2. Durometer Measurement (Comparative Examples 2-1 to 2-4)

The hardness was measured using a Type A durometer in conformity with JIS K6253.

TABLE 2

| | | SANS (Formula 2-2 to Formula 2-5) | | | | | | | |
|---|---|---|---|---|---|---|---|---|---|
| | | Examples | | | | Comparative Examples | | | |
| | | 2-1 | 2-2 | 2-3 | 2-4 | 2-1 | 2-2 | 2-3 | 2-4 |
| Composition | BR730 | 100 | 100 | 100 | 100 | 100 | 100 | 100 | 100 |
| | SANCELER SR | 30 | 30 | 30 | 25 | 30 | 30 | 30 | 25 |
| | PERCUMYL D | 1 | 0.75 | 0.75 | 1.5 | 1 | 0.75 | 0.75 | 1.5 |
| | TN | 0.54 | — | — | — | 0.54 | — | — | — |
| | DPDS | — | 0.5 | — | — | — | 0.5 | — | — |
| | PCTP | — | — | 0.63 | — | — | — | 0.63 | — |
| | 2.6-DCTP | — | — | — | 0.32 | — | — | — | 0.32 |
| Method for evaluating hardness | SANS measurement | 100 | 92 | 85 | 71 | — | — | — | — |
| | Durometer measurement | — | — | — | — | 89 | 89 | 89 | 89 |

As shown in Table 2, it was proved that the hardness can be evaluated by determining the G and N values by curve fitting with Formula 2-2 to Formula 2-5 in Examples 2-1 to 2-4 which are based on SANS measurement. In particular, the comparison with the corresponding Comparative Examples 2-1 to 2-4 shows that SANS measurement can accurately measure even a slight difference in hardness between samples between which the difference is difficult to evaluate by durometer measurement. Further, the SANS measurement was found to have less variation between measurements and to be capable of evaluating the hardness with high measurement accuracy and good reproducibility.

Examples 3-1 to 3-16 and Comparative Examples 3-1 to 3-10

Synthesis of Monomer (1)

A 100-ml container sufficiently purged with nitrogen was charged with cyclohexane (50 ml), pyrrolidine (4.1 ml), and divinylbenzene (8.9 ml). Then, n-butyllithium 1.6 M in hexane (0.7 ml) was added thereto at 0° C. and the mixture was stirred. After one hour, isopropanol was added to terminate the reaction. The mixture was extraction-purified, thereby providing a monomer (1).
(Synthesis of Polymer (1))

A 1000-ml pressure-resistant container sufficiently purged with nitrogen was charged with cyclohexane (600 ml), styrene (12.6 ml), butadiene (71.0 ml), the monomer (1) (0.06 g), and tetramethylethylenediamine (0.11 ml). Then, n-butyllithium 1.6 M in hexane (0.2 ml) was added thereto at 40° C. and the mixture was stirred. After three hours, a modifier (0.5 ml) was added and the mixture was stirred. After one hour, isopropanol (3 ml) was added to terminate the polymerization. To the reaction solution was added 2,6-tert-butyl-p-cresol (1 g). The mixture was then subjected to reprecipitation with methanol. The precipitate was heated and dried, thereby providing a polymer (1).
(Synthesis of Polymer (2))

A polymer (2) was obtained in the same manner as mentioned for the polymer (1), except that the amount of the monomer (1) was 0.17 g.
(Synthesis of Polymer (3))

A polymer (3) was obtained in the same manner as mentioned for the polymer (1), except that the amount of the monomer (1) was 0.29 g.
(Preparation of Molded Product)

According to each of the compositions shown in Tables 3-1 to 3-4, the materials were kneaded using a Banbury mixer and a roll kneader. Then, the kneaded mixture was press-molded at 170° C. for 20 minutes to provide a molded product.

The energy loss in the molded products thus obtained was evaluated by the following SAXS measurement, SANS measurement, and dynamic viscoelasticity analysis. The results are shown below.

3-1. SAXS Measurement (Examples 3-1 to 3-6, Examples 3-11 to 3-16)

(1) Radius of Gyration $R_g$

An about 1-mm-thick plate-like sample (molded product) was mounted on a sample holder, and the sample was irradiated with X-rays at room temperature. A scattering intensity curve obtained by the measurement with BL03XU and a scattering intensity curve obtained by the measurement with BL20XU were combined by least squares. These two curves were combined as follows: the scattering intensity curve obtained using BL03XU at wider angles was fixed, and the scattering intensity curve obtained using BL20XU at smaller angles was then shifted. The scattering intensity curve $I_{(q)}$ obtained was curve fitted with Formula 3-2 and Formula 3-3, and the fitting parameter $R_g$ (the radius of gyration of 1 nm to 100 μm) was then determined by least squares. The reciprocal of the radius of gyration $R_g$ obtained is expressed as an index relative to that of Example 3-1 or Example 3-11 (=100). A higher index indicates a lower energy loss.

In Examples 3-11 to 3-13, a plate-like sample was preliminarily subjected to extraction with an acidic solvent mixture to reduce (remove) the amount of a metal and a metal compound in the sample, using a Soxhlet extractor under the following conditions, and then the sample was subjected to the SAXS measurement.
(Conditions)
Extraction temperature: 60° C.
Extraction time: 60 hours
Acidic solvent mixture: 6 N hydrochloric acid/acetone solvent mixture (mixture ratio=3/7)
(2) Number N The scattering intensity curve $I_{(q)}$ obtained was curve fitted with Formula 3-2 to Formula 3-5, and the fitting parameter G was then determined by least squares. A value of $3.8 \times 10^{23}$ (electron·cm$^{-3}$) was used as the difference σ in electron density of a silica-blended material to determine the number N of scatterers (clusters with a radius of gyration $R_g$ of 1 nm to 100 μm) per unit volume. The reciprocal of the number N obtained is expressed as an index relative to that of Example 3-4 (=100). A higher index indicates a lower energy loss.
(SAXS Apparatus)

SAXS: SAXS measurement apparatus provided with the beamlines BL03XU and BL20XU of the large synchrotron radiation facility "SPring-8" belonging to Japan Synchrotron Radiation Research Institute
(Measurement Conditions)
Brilliance of X-rays: $5 \times 10^{12}$ photons/s/mrad$^2$/mm$^2$/0.1% bw
Number of photons in X-rays: $2 \times 10^9$ photons/s
Energy of X-rays: 8 keV (BL03XU), 23 keV (BL20XU)
Distance between sample and detector: 3 m (BL03XU), 160 m (BL20XU)
(Detector)
Two-dimensional detector (image intensifier and CCD camera)

3-2. SANS Measurement (Examples 3-7 to 3-10)

An about 1-mm-thick plate-like sample (molded product) was swollen to equilibrium in deuterated toluene and mounted on a sample holder, and the sample was irradiated with neutrons at room temperature. Absolute scattering intensity curves obtained by measuring the sample at distances of 2.5 m and 10 m from the detector and with a focusing lens were combined by least squares. These three curves were combined as follows: the scattering intensity curve obtained by measuring the sample at a distance of 2.5 m from the detector was fixed, and the scattering intensity curves obtained by measuring the sample at a distance of 10 m and with a focusing lens were then shifted. The scattering intensity curve $I_{(q)}$ obtained was curve fitted with Formula 3-2 and Formula 3-3, and the fitting parameter $R_g$ (the radius of gyration of 1 nm to 100 μm) was then determined by least squares. The reciprocal of the radius of gyration $R_g$ obtained is expressed as an index relative to that of Example 3-7 (=100). A higher index indicates a lower energy loss.

(SANS Apparatus)

SANS: SANS measurement apparatus provided with the SANS-J beamline at the JRR-3 research reactor belonging to Japan Atomic Energy Agency, Independent Administrative Agency (Measurement Conditions)

Wavelength of neutrons: 6.5 Å

Flux density of neutrons: $9.9 \times 10^7$ neutrons/cm$^2$/s

Distance between sample and detector: 2.5 m and 10 m (in order to obtain the information at smaller angles, the sample was also measured at a distance of 10 m from the detector, using a focusing lens.)

(Detector)

Two-dimensional detector ($^3$He two-dimensional detector and two-dimensional photomultiplier+ZnS/$^6$LiF detector)

3-3. Dynamic Viscoelasticity Analysis
(Comparative Examples 3-1 to 3-10)

With a spectrometer (Ueshima Seisakusho Co., Ltd.), tan δ was measured at a dynamic strain amplitude of 1%, a frequency of 10 Hz, and a temperature of 60° C. The reciprocal of the tan δ value obtained is expressed as an index relative to that of Comparative Example 3-1, Comparative Example 3-4, or Comparative Example 3-8 (~100). A higher index indicates a lower energy loss.

3-4. Tire Rolling Performance

Test tires were formed from tire components based on the compositions in Examples 3-11 to 3-16 and Comparative Examples 3-8 to 3-10, and the tires were run on a rolling resistance tester with a rim (15×6JJ) at an internal pressure of 230 kPa, a load of 3.43 kN, and a speed of 80 km/h, to measure the rolling resistance. The rolling resistance measured is expressed as an index relative to that of Example 3-11 (=100). A higher index indicates better rolling performance and a lower energy loss in tires.

TABLE 3-1

| | | SAXS (Formula 3-2 and Formula 3-3) | | | | | |
|---|---|---|---|---|---|---|---|
| | | Examples | | | Comparative Examples | | |
| | | 3-1 | 3-2 | 3-3 | 3-1 | 3-2 | 3-3 |
| Composition | NR | 30 | 30 | 30 | 30 | 30 | 30 |
| | Polymer (1) | 70 | — | — | 70 | — | — |
| | Polymer (2) | — | 70 | — | — | 70 | — |
| | Polymer (3) | — | — | 70 | — | — | 70 |
| | Silica | 75 | 75 | 75 | 75 | 75 | 75 |
| | Silane coupling agent | 5 | 5 | 5 | 5 | 5 | 5 |
| | Aromatic oil | 20 | 20 | 20 | 20 | 20 | 20 |
| | Stearic acid | 2 | 2 | 2 | 2 | 2 | 2 |
| | Antioxidant | 1 | 1 | 1 | 1 | 1 | 1 |
| | Wax | 1 | 1 | 1 | 1 | 1 | 1 |
| | Sulfur | 1.5 | 1.5 | 1.5 | 1.5 | 1.5 | 1.5 |
| | Vulcanization accelerator (1) | 1 | 1 | 1 | 1 | 1 | 1 |
| | Vulcanization accelerator (2) | 0.5 | 0.5 | 0.5 | 0.5 | 0.5 | 0.5 |
| Energy loss index | SAXS measurement | 100 | 105 | 111 | — | — | — |
| | Dynamic viscoelasticity analysis | — | — | — | 100 | 100 | 101 |

As shown in Table 3-1, it was proved that the energy loss can be evaluated by determining the $R_g$ value by curve fitting with Formula 3-2 and Formula 3-3 in Examples 3-1 to 3-3 which are based on SAXS measurement. In particular, the comparison with Comparative Examples 3-1 to 3-3 shows that SAXS measurement can accurately measure even a slight difference in energy loss between samples between which the difference is difficult to evaluate by dynamic viscoelasticity analysis.

TABLE 3-2

| | | SAXS (Formula 3-2 to Formula 3-5) | | | | | |
|---|---|---|---|---|---|---|---|
| | | Examples | | | Comparative Examples | | |
| | | 3-4 | 3-5 | 3-6 | 3-1 | 3-2 | 3-3 |
| Composition | NR | 30 | 30 | 30 | 30 | 30 | 30 |
| | Polymer (1) | 70 | — | — | 70 | — | — |
| | Polymer (2) | — | 70 | — | — | 70 | — |
| | Polymer (3) | — | — | 70 | — | — | 70 |
| | Silica | 75 | 75 | 75 | 75 | 75 | 75 |
| | Silane coupling agent | 5 | 5 | 5 | 5 | 5 | 5 |
| | Aromatic oil | 20 | 20 | 20 | 20 | 20 | 20 |

TABLE 3-2-continued

| | | SAXS (Formula 3-2 to Formula 3-5) | | | | | |
|---|---|---|---|---|---|---|---|
| | | Examples | | | Comparative Examples | | |
| | | 3-4 | 3-5 | 3-6 | 3-1 | 3-2 | 3-3 |
| | Stearic acid | 2 | 2 | 2 | 2 | 2 | 2 |
| | Antioxidant | 1 | 1 | 1 | 1 | 1 | 1 |
| | Wax | 1 | 1 | 1 | 1 | 1 | 1 |
| | Sulfur | 1.5 | 1.5 | 1.5 | 1.5 | 1.5 | 1.5 |
| | Vulcanization accelerator (1) | 1 | 1 | 1 | 1 | 1 | 1 |
| | Vulcanization accelerator (2) | 0.5 | 0.5 | 0.5 | 0.5 | 0.5 | 0.5 |
| Energy loss index | SAXS measurement | 100 | 129 | 194 | — | — | — |
| | Dynamic viscoelasticity analysis | — | — | — | 100 | 100 | 101 |

From the results in Examples 3-4 to 3-6 in Table 3-2, it was demonstrated that a slight difference in energy loss can be more accurately measured by determining the number N by curve fitting with Formula 3-2 to Formula 3-5.

TABLE 3-3

| | | SANS (Formula 3-2 and Formula 3-3) | | | | | | | |
|---|---|---|---|---|---|---|---|---|---|
| | | Examples | | | | Comparative Examples | | | |
| | | 3-7 | 3-8 | 3-9 | 3-10 | 3-4 | 3-5 | 3-6 | 3-7 |
| Composition | BR730 | 100 | 100 | 100 | 100 | 100 | 100 | 100 | 100 |
| | SANCELER SR | 30 | 30 | 30 | 25 | 30 | 30 | 30 | 25 |
| | PERCUMYL D | 1 | 0.75 | 0.75 | 1.5 | 1 | 0.75 | 0.75 | 1.5 |
| | TN | 0.52 | — | — | — | 0.52 | — | — | — |
| | DPDS | — | 0.5 | — | — | — | 0.5 | — | — |
| | PCTP | — | — | 0.65 | — | — | — | 0.65 | — |
| | 2,6-DCTP | — | — | — | 0.36 | — | — | — | 0.36 |
| Energy loss index | SANS measurement | 100 | 110 | 118 | 135 | — | — | — | — |
| | Dynamic viscoelasticity analysis | — | — | — | — | 100 | 100 | 100 | 101 |

As shown in Table 3-3, it was proved that the energy loss can also be evaluated by determining the $R_g$ value by curve fitting with Formula 3-2 and Formula 3-3 in Examples 3-7 to 3-10 which are based on SANS measurement. In particular, the comparison with the corresponding Comparative Examples 3-4 to 3-7 shows that SANS measurement can accurately measure a slight difference in energy loss. Further, that the SAXS measurement and the SANS measurement in Tables 3-1 to 3-3 were found to have less variation between measurements and to be capable of evaluating the energy loss with high measurement accuracy and good reproducibility.

TABLE 3-4

| | | SAXS (Formula 3-2 and Formula 3-3) | | | | | | | | |
|---|---|---|---|---|---|---|---|---|---|---|
| | | Examples | | | | | | Comparative Examples | | |
| | | 3-11 | 3-12 | 3-13 | 3-14 | 3-15 | 3-16 | 3-8 | 3-9 | 3-10 |
| Composition | NR | 30 | 30 | 30 | 30 | 30 | 30 | 30 | 30 | 30 |
| | Polymer (1) | 70 | — | — | 70 | — | — | 70 | — | — |
| | Polymer (2) | — | 70 | — | — | 70 | — | — | 70 | — |
| | Polymer (3) | — | — | 70 | — | — | 70 | — | — | 70 |
| | Silica | 75 | 75 | 75 | 75 | 75 | 75 | 75 | 75 | 75 |
| | Silane coupling agent | 5 | 5 | 5 | 5 | 5 | 5 | 5 | 5 | 5 |
| | Aromatic oil | 20 | 20 | 20 | 20 | 20 | 20 | 20 | 20 | 20 |
| | Stearic acid | 2 | 2 | 2 | 2 | 2 | 2 | 2 | 2 | 2 |
| | Zinc oxide | 3 | 3 | 3 | 3 | 3 | 3 | 3 | 3 | 3 |
| | Antioxidant | 1 | 1 | 1 | 1 | 1 | 1 | 1 | 1 | 1 |
| | Wax | 1 | 1 | 1 | 1 | 1 | 1 | 1 | 1 | 1 |
| | Sulfur | 1.5 | 1.5 | 1.5 | 1.5 | 1.5 | 1.5 | 1.5 | 1.5 | 1.5 |
| | Vulcanization accelerator (1) | 1 | 1 | 1 | 1 | 1 | 1 | 1 | 1 | 1 |
| | Vulcanization accelerator (2) | 0.5 | 0.5 | 0.5 | 0.5 | 0.5 | 0.5 | 0.5 | 0.5 | 0.5 |

TABLE 3-4-continued

| | | SAXS (Formula 3-2 and Formula 3-3) | | | | | | | | |
|---|---|---|---|---|---|---|---|---|---|---|
| | | Examples | | | | | | Comparative Examples | | |
| | | 3-11 | 3-12 | 3-13 | 3-14 | 3-15 | 3-16 | 3-8 | 3-9 | 3-10 |
| Energy loss index | SAXS measurement (with treatment with acidic solvent mixture) | 100 | 129 | 194 | — | — | — | — | — | — |
| | SAXS measurement (without treatment with acidic solvent mixture) | — | — | — | 100 | 103 | 106 | — | — | — |
| | Dynamic viscoelasticity analysis | — | — | — | — | — | — | 100 | 100 | 101 |
| | Tire rolling performance | 100 | 108 | 124 | 100 | 108 | 124 | 100 | 108 | 124 |

As shown in Table 3-4, it was proved that with respect to the compositions containing zinc oxide in the SAXS measurement-based examples, the energy loss can be more accurately evaluated in Examples 3-11 to 3-13 including a treatment with an acidic solvent mixture, as compared to in Examples 3-14 to 3-16 without such treatment. The SAXS measurement was also found to be capable of evaluating polymer materials containing a metal and/or a metal compound with high accuracy.

The invention claimed is:

1. A method for evaluating rebound resilience of a polymer material, comprising the steps of:
   irradiating the polymer material with X-rays or neutrons performing X-ray scattering measurement or neutron scattering measurement of the polymer material to obtain a scattering intensity curve I(q);
   determining a radius of gyration $R_{g1}$ by curve fitting Formula 1-2 and Formula 1-3 to the scattering intensity curve $I_{(q)}$;
   evaluating rebound resilience based on the radius of gyration $R_{g1}$ using a relationship that the rebound resilience increases as the radius of gyration $R_{g1}$ decreases, $$q = \frac{4\pi \sin(\theta/2)}{\lambda} \quad \text{Formula 1-1}$$

wherein $\theta$ is a scattering angle; and $\lambda$ is a wavelength of X-rays or neutrons, $$I_{(q)} = P_1\left[\left\{\mathrm{erf}\left(\frac{qR_{g0}}{\sqrt{6}}\right)^3 \bigg/ q\right\}\right]^{D_{f1}} \exp\left(\frac{-q^2 R_{g1}^2}{3}\right) + G_1 \exp\left(\frac{-q^2 R_{g1}^2}{3}\right) + P_2\left[\left\{\mathrm{erf}\left(\frac{qR_{g1}}{\sqrt{6}}\right)^3 \bigg/ q\right\}\right]^{D_{f2}}, \quad \text{Formula 1-2}$$

$$\mathrm{erf}(z) = \frac{2}{\sqrt{\pi}} \int_0^z e^{-t^2} dt \quad \text{Formula 1-3}$$

wherein $P_1$, $P_2$, $G_1$, $R_{g0}$, $R_{g1}$, $D_{f1}$, and $D_{f2}$ are fitting parameters; q is as defined above Formula 1-1; and z and t are any positive numbers.

2. The method for evaluating rebound resilience of a polymer material according to claim 1,
   wherein the X-ray scattering measurement is small-angle X-ray scattering measurement and the neutron scattering measurement is small-angle neutron scattering measurement.

3. The method for evaluating rebound resilience of a polymer material according to claim 2,
   wherein the polymer material contains at least one metal-coordinating functional group in its molecular structure.

4. The method for evaluating rebound resilience of a polymer material according to claim 2,
   wherein the measurement is performed using the X-rays or neutrons under conditions where q is in a range of not more than 10 nm$^{-1}$.

5. The method for evaluating rebound resilience of a polymer material according to claim 1,
   wherein the polymer material contains at least one metal-coordinating functional group in its molecular structure.

6. The method for evaluating rebound resilience of a polymer material according to claim 1,
   wherein the measurement is performed using the X-rays or neutrons under conditions where q is in a range of not more than 10 nm nm$^{-1}$.

7. A method for evaluating hardness of a polymer material, comprising the steps of:
   irradiating the polymer material with X-rays or neutrons performing X-ray scattering measurement or neutron scattering measurement of the polymer material-to obtain a scattering intensity curve I(q);
   determining a radius of gyration Rg of 1 nm to 100 μm by curve fitting Formula 2-2 and Formula 2-3 to the scattering intensity curve $I_{(q)}$;
   evaluating hardness based on the radius of gyration Rg using a relationship that the hardness increases as the radius of gyration $R_g$ decreases, $$q = \frac{4\pi \sin(\theta/2)}{\lambda} \quad \text{Formula 2-1}$$

wherein $\theta$ is a scattering angle; and $\lambda$ is a wavelength of X-rays or neutrons, $$I_{(q)} = \sum_{i=1}^{n} \left\{ P_i\left[\left\{\mathrm{erf}\left(\frac{qR_{gi}}{\sqrt{6}}\right)^3 \bigg/ q\right\}\right]^{D_{fi}} \exp\left(\frac{-q^2 R_{g(i+1)}^2}{3}\right) + G_i \exp\left(\frac{-q^2 R_{g(i+1)}^2}{3}\right) \right\} + P_{n+1}\left[\left\{\mathrm{erf}\left(\frac{qR_{g(n+1)}}{\sqrt{6}}\right)^3 \bigg/ q\right\}\right]^{D_{f(n+1)}}, \quad \text{Formula 2-2}$$

$$\text{erf}(z) = \frac{2}{\sqrt{\pi}} \int_0^z e^{-t^2} dt \qquad \text{Formula 2-3}$$

wherein $P_i$, $G_i$, $R_{gi}$, and $D_{fi}$ are fitting parameters; n is an integer; q is as defined above Formula 2-1; and z and t are any positive numbers.

8. The method for evaluating hardness of a polymer material according to claim 7, wherein the X-ray scattering measurement is small-angle X-ray scattering measurement and the neutron scattering measurement is small-angle neutron scattering measurement.

9. The method for evaluating hardness of a polymer material according to claim 7, wherein the polymer material is a rubber material formed from one or more conjugated diene compounds.

10. The method for evaluating hardness of a polymer material according to claim 9,
wherein the rubber material is a rubber material for tires.

11. The method for evaluating hardness of a polymer material according to claim 7,
wherein the measurement is performed using the X-rays or neutrons under conditions where q is in a range of not more than 10 nm$^{-1}$.

12. A method for evaluating hardness of a polymer material, comprising
irradiating the polymer material with X-rays or neutrons performing X-ray scattering measurement or neutron scattering measurement of the polymer material to obtain a scattering intensity curve I(q);
determining a number N per unit volume of scatterers having a radius of gyration $R_g$ of 1 nm to 100 μm by curve fitting Formula 2-2 to Formula 2-5 to the scattering intensity curve $I_{(q)}$;
evaluating hardness based on the number N using a relationship that the hardness increases as the number N increases, $$q = \frac{4\pi \sin(\theta/2)}{\lambda} \qquad \text{Formula 2-1}$$

wherein θ is a scattering angle; and λ is a wavelength of X-rays or neutrons, $$I_{(q)} = \sum_{i=1}^{n} \left\{ P_i \left[ \left\{ \text{erf}\left(\frac{qR_{gi}}{\sqrt{6}}\right)^3 / q \right\} \right]^{D_{fi}} \exp\left(\frac{-q^2 R_{g(i+1)}^2}{3}\right) + \right.$$

$$G_i \exp\left(\frac{-q^2 R_{g(i+1)}^2}{3}\right) \right\} +$$

$$P_{n+1} \left[ \left\{ \text{erf}\left(\frac{qR_{g(n+1)}}{\sqrt{6}}\right)^3 / q \right\} \right]^{D_{f(n+1)}}, \qquad \text{Formula 2-2}$$

$$\text{erf}(z) = \frac{2}{\sqrt{\pi}} \int_0^z e^{-t^2} dt, \qquad \text{Formula 2-3}$$

$$G_i = N_i (\sigma V_i)^2, \qquad \text{Formula 2-4}$$

$$V_i = \frac{4}{3}\pi \left(\sqrt{\frac{5}{3}} R_{gi}\right)^3 \qquad \text{Formula 2-5}$$

wherein $P_i$, $G_i$, $R_{gi}$, and $D_{fi}$ are fitting parameters; $N_i$ is a number of scatterers per unit volume (N/cm$^3$); $V_i$ is a volume of scatterer having the radius of gyration $R_{gi}$; n is an integer; q is as defined above Formula 2-1; z and t are any positive numbers; and σ is a difference in electron density (electron·cm$^{-3}$) between a scatterer and a surrounding matrix material, or a difference in scattering length density (cm$^{-2}$) between a scatterer and a surrounding deuterated solvent.

13. A method for evaluating energy loss in a polymer material, comprising
irradiating the polymer material with X-rays or neutrons performing X-ray scattering measurement or neutron scattering measurement of the polymer material to obtain a scattering intensity curve I(q);
determining a radius of gyration $R_g$ of 1 nm to 100 μm by curve fitting Formula 3-2 and Formula 3-3 to the scattering intensity curve $I_{(q)}$;
evaluating energy loss based on the radius of gyration $R_g$ using a relationship that the energy loss decreases as the radius of gyration $R_g$ decreases, $$q = \frac{4\pi \sin(\theta/2)}{\lambda} \qquad \text{Formula 3-1}$$

wherein θ is a scattering angle; and λ is a wavelength of X-rays or neutrons, $$I_{(q)} = \sum_{i=1}^{n} \left\{ P_i \left[ \left\{ \text{erf}\left(\frac{qR_{gi}}{\sqrt{6}}\right)^3 / q \right\} \right]^{D_{fi}} \exp\left(\frac{-q^2 R_{g(i+1)}^2}{3}\right) + \right. \qquad \text{Formula 3-2}$$

$$G_i \exp\left(\frac{-q^2 R_{g(i+1)}^2}{3}\right) \right\} +$$

$$P_{n+1} \left[ \left\{ \text{erf}\left(\frac{qR_{g(n+1)}}{\sqrt{6}}\right)^3 / q \right\} \right]^{D_{f(n+1)}},$$

$$\text{erf}(z) = \frac{2}{\sqrt{\pi}} \int_0^z e^{-t^2} dt \qquad \text{Formula 3-3}$$

wherein $P_i$, $G_i$, $R_{gi}$, and $D_{fi}$ are fitting parameters; n is an integer; q is as defined above Formula 3-1; and z and t are any positive numbers.

14. The method for evaluating energy loss in a polymer material according to claim 13, wherein the X-ray scattering measurement is small-angle X-ray scattering measurement and the neutron scattering measurement is small-angle neutron scattering measurement.

15. The method for evaluating energy loss in a polymer material according to claim 13, wherein the polymer material is a rubber material formed from one or more conjugated diene compounds.

16. The method for evaluating energy loss in a polymer material according to claim 15, wherein the rubber material is a rubber material for tires.

17. The method for evaluating energy loss in a polymer material according to claim 13,
wherein the polymer material is a material in which an amount of at least one of a metal and a metal compound is reduced.

18. The method for evaluating energy loss in a polymer material according to claim 13, wherein the polymer material is a material in which an amount of at least one of a metal and a metal compound is reduced using an acidic solvent.

19. The method for evaluating energy loss in a polymer material according to claim 13, wherein the measurement is performed using the X-rays or neutrons under conditions where q is in a range of not more than 10 nm$^{-1}$.

20. A method for evaluating energy loss in a polymer material, comprising irradiating the polymer material with X-rays or neutrons performing X-ray scattering measurement or neutron scattering measurement of the polymer material to obtain a scattering intensity curve I(q);

determining a number N per unit volume of scatterers having a radius of gyration Rg of 1 nm to 100 μm by curve fitting Formula 3-2 to Formula 3-5 to the scattering intensity curve $I_{(q)}$;

evaluating energy loss based on the number N using a relationship that the energy loss decreases as the number N decreases, $$q = \frac{4\pi \sin(\theta/2)}{\lambda} \quad \text{Formula 3-1}$$

wherein θ is a scattering angle; and λ is a wavelength of X-rays or neutrons, $$I_{(q)} = \sum_{i=1}^{n} \left\{ P_i \left[ \left\{ \mathrm{erf}\left(\frac{qR_{gi}}{\sqrt{6}}\right)^3 \Big/ q \right\} \right]^{D_{fi}} \exp\left(\frac{-q^2 R_{g(i+1)}^2}{3}\right) + \right. $$
$$\left. G_i \exp\left(\frac{-q^2 R_{g(i+1)}^2}{3}\right) \right\} + $$
$$P_{n+1} \left[ \left\{ \mathrm{erf}\left(\frac{qR_{g(n+1)}}{\sqrt{6}}\right)^3 \Big/ q \right\} \right]^{D_{f(n+1)}}, \quad \text{Formula 3-2}$$

$$\mathrm{erf}(z) = \frac{2}{\sqrt{\pi}} \int_0^z e^{-t^2} dt, \quad \text{Formula 3-3}$$

$$G_i = N_i(\sigma V_i)^2, \quad \text{Formula 3-4}$$

$$V_i = \frac{4}{3}\pi \left(\sqrt{\frac{5}{3}} R_{gi}\right)^3 \quad \text{Formula 3-5}$$

wherein $P_i$, $G_i$, $R_{gi}$, and $D_{fi}$ are fitting parameters; $N_i$ is a number of scatterers per unit volume (N/cm$^3$); $V_i$ is a volume of scatterer having the radius of gyration $R_{gi}$; n is an integer; q is as defined above Formula 3-1; z and t are any positive numbers; and σ is a difference in electron density (electron·cm$^{-3}$) between a scatterer and a surrounding matrix material, or a difference in scattering length density (cm$^{-2}$) between a scatterer and a surrounding deuterated solvent.

* * * * *